(12) United States Patent
Simon et al.

(10) Patent No.: US 7,294,107 B2
(45) Date of Patent: Nov. 13, 2007

(54) STANDARDIZED MEDICAL COGNITIVE ASSESSMENT TOOL

(75) Inventors: Ely S. Simon, Bayside, NY (US); Glen M. Doniger, Houston, TX (US)

(73) Assignee: NeuroTrax Corporation, Newark, NJ (US)

( * ) Notice: Subject to any disclaimer, the term of this patent is extended or adjusted under 35 U.S.C. 154(b) by 335 days.

(21) Appl. No.: 10/971,067

(22) Filed: Oct. 25, 2004

(65) Prior Publication Data

US 2005/0187436 A1    Aug. 25, 2005

Related U.S. Application Data

(63) Continuation-in-part of application No. PCT/IL2004/000184, filed on Feb. 24, 2004.

(51) Int. Cl.
*A61B 5/00* (2006.01)

(52) U.S. Cl. .................. 600/300; 434/236
(58) Field of Classification Search ........ 600/300–301, 600/544–545; 434/236–238; 128/920
See application file for complete search history.

(56) References Cited

U.S. PATENT DOCUMENTS

| | | | |
|---|---|---|---|
| 4,712,562 A | 12/1987 | Ohayon | |
| 5,295,491 A | 3/1994 | Gevins | |
| 6,280,198 B1 | 8/2001 | Calhoun et al. | |
| 6,416,472 B1 | 7/2002 | Cady | |
| 6,435,878 B1 | 8/2002 | Reynolds et al. | |
| 6,475,161 B2 | 11/2002 | Teicher et al. | |
| 6,565,359 B2 | 5/2003 | Calhoun et al. | |
| 6,632,174 B1 | 10/2003 | Breznitz | |
| 6,669,481 B2 | 12/2003 | Winter et al. | |
| 6,820,037 B2 | 11/2004 | Simon | |
| 6,964,638 B2 | 11/2005 | Theodoracopulos | |
| 2001/0029322 A1 | 10/2001 | Illiff | |
| 2001/0034615 A1 | 10/2001 | Wilkinson | |
| 2002/0029157 A1 | 3/2002 | Marchosky | |
| 2002/0192624 A1 | 12/2002 | Darby | |
| 2003/0073885 A1 | 4/2003 | Theodoracopulos | |

OTHER PUBLICATIONS

R. Swainson et al., "Early Detection and Differential Diagnosis of Alzheimer's Disease and Depression with Neuropsychological Tasks", Dementia and Geriatric Cognitive Disorders, Jul.-Aug. 2001 12(4): 265-80.
Keith M. S. et al., "Validity of a cognitive computerized assessment system in brain-injured patients", Brain Injury, Dec. 1998, pp. 1037-1043, vol. 12, No. 12.
Elwood R., MicroCog Assessment of Cognitive Functioning, Neuropsychology Review, 2001, vol. 11, No. 2.
http://www.otwesten.de/scaletrans/index.htm.

*Primary Examiner*—Max F Hindenburg
*Assistant Examiner*—Michael C Astorino
(74) *Attorney, Agent, or Firm*—AlphaPatent Associates Ltd.; Rochel L. Abboudi; Daniel J. Swirsky

(57) ABSTRACT

A testing system and method for evaluation of neurological function are provided. Specifically, the system and method can be used to differentiate between normal and pathological function for motor skills, logic, reasoning, coordination, verbal function, memory, and various other skills. In addition, it is designed to provide a package to a clinician, including a recommended battery of tests and a results report. The system and method described herein is designed to reduce bias due to the human nature of the tester, while still maintaining versatility, individualized attention and depth of analysis in testing.

8 Claims, 10 Drawing Sheets

STANDARDIZED MEDICAL COGNITIVE ASSESSMENT TOOL

CROSS-REFERENCES TO RELATED APPLICATIONS

The present application is a continuation-in-part of PCT patent application Ser. No. PCT/IL04/00184 filed on Feb. 24, 2004, which claims the benefit of U.S. patent application Ser. No. 10/370,463, filed on Feb. 24, 2003, the disclosures of which are incorporated herein by reference in their entireties for all purposes.

FIELD AND BACKGROUND OF THE INVENTION

The present invention relates to a standardized medical cognitive assessment tool. More specifically, the present invention relates to systems and methods for testing and evaluating cognitive ability that are particularly sensitive to mild cognitive impairment and are suitable for a variety of challenging groups, including the elderly, children, people with learning disorders or short attention spans, the mildly visually impaired, and others. The systems and methods described are a tool for a clinician to be able to track cognitive ability and diagnose mental conditions such as Alzheimer's or other forms of dementia, attention deficit disorder, or learning disorders.

Cognition is a general term for mental processes by which an individual acquires knowledge, solves problems, and plans activities. Cognitive skills include attention, visual/spatial perception, judging and decision-making, problem solving, memory and verbal function, among others. The functional levels of each of these skills can be studied alone or in combination for a particular individual.

Evaluation and quantification of cognitive ability has been a challenge to both scientists and clinicians. This information is important for enabling quick and accurate diagnoses, for directing treatments, and for tracking the patient's response to medical, surgical, or rehabilitation therapies. Particularly in the clinical arena, testing systems have been subject to problems of bias, both from the external environment and from individuals administering the tests. External biases may include language or culture gaps between the test content and the subject taking the test, or lack of familiarity with the mechanical aspects of the test, or any other external factor that may influence test taking ability. Potential biases from a test administrator include conversation between the administrator and the subject, or subjective observations by the administrator which may play a role in score determination. Furthermore, tests are typically administered without adequate consideration of the skill level of the subject being tested. The result of this type of oversight may be a test which is too easy or too difficult for a particular individual, causing "ceiling" or "floor" effects which essentially eliminate meaningful results. This effect is particularly apparent for mildly impaired individuals, for whom the testing scheme is too complex, either in terms of stimulus and response interfaces, or in terms of the level of questions. In addition, traditional tests cannot accurately judge reaction time, which is a factor that should be considered in evaluation of many cognitive skills. Generally, it would be desirable to be able to evaluate several aspects simultaneously and retain the option of scoring based on each of the skills being tested alone or in combination.

Most tests that are designed to measure cognitive skill level, such as IQ tests, merely measure function and provide a score. However, current testing systems do not evaluate the borderline region of functional ability which can indicate a normal versus a pathological state. For example, those with "mild cognitive impairment" whose level of cognitive function is transitional between normal and dementia are often not diagnosed in a systematic and reliable way. Furthermore, different levels of probability of various cognitive states are not provided. It would be desirable to have an objective testing system with specific multi-level criteria for determining whether intervention would be necessary or helpful.

Prior art testing systems have been developed to provide an interactive computerized way of measuring cognitive skills. U.S. Pat. No. 6,435,878 to Reynolds et al. discloses an interactive computer program for measuring and analyzing mental ability. Reynolds et al. disclose a system which presents a variety of auditory or visual stimuli, and interactively provides feedback and adjusts the level of the test based on received responses. The system tests for reaction time, memory, attention and decision-making processes. However, it is not a clinical tool which would be useful for a clinician in providing diagnostic information related to skill level or pathological state. Prior art systems such as the one disclosed in Reynolds et al. do not sufficiently expand the range of sensitivity to avoid ceiling or floor effects in mildly impaired individuals.

A neurological testing apparatus is described in U.S. Pat. No. 6,517,480 to Krass. This apparatus includes a microprocessing unit for carrying out test procedures, an interface to a sensory signal generating device, an interface to a reaction detecting device, and an interface to a memory for reading test procedures stored in the memory. The apparatus tests for abstract reasoning ability, visual memory, visual/motor perception, response time and grip strength. However, the apparatus lacks at least the following features: automated adaptability, utility for mildly visually impaired individuals, and a coherent reporting and analysis system.

Furthermore, the prior art systems do not provide tools for assessing individuals based on probabilities and sub-ranges of normal and abnormal diagnoses.

There is thus a widely recognized need for, and it would be highly advantageous to have, a testing system and method devoid of the above limitations.

SUMMARY OF THE INVENTION

According to one aspect of the invention, there is provided a diagnostic tool for determining a cognitive state of a subject. The tool includes a battery of tests for measuring a neurological parameter, an interface allowing a clinician to access the battery of tests and administer the battery of tests to a subject, the subject generating data in response to the administered battery of tests, a processor for processing the generated data, and a report generated by the processor and based on the generated data, wherein the report provides a view of the data within ranges and sub-ranges of cognitive ability.

According to another aspect of the invention, there is provided a method for providing a report to a clinician. The method includes obtaining an index score for a cognitive skill, graphing the index score in relation to a set of cutoff numbers, wherein the cutoff numbers define ranges and sub-ranges of cognitive ability, and presenting the graphed index scores in a report format to the clinician.

According to yet another aspect of the invention, there is provided a method for providing sub-ranges of cognitive ability. The method includes providing a standard determination of cognitive ability to an individual, administering a battery of tests designed to measure cognitive ability to the individual, determining a cognitive ability of the individual based on results of the battery of tests at each of several spread values, comparing the determined cognitive ability with the standard determination so as to collect a comparison measure at the several spread values, repeating the providing, administering, determining and comparing until multiple comparison measures are collected, optimizing the multiple comparison measures and choosing a set of cutoff spread values based on the optimization.

According to yet another aspect of the invention, there is provided a method for determining a set of sub-ranges of a cognitive determination. The method includes comparing data from a standard determination with data from a testing scheme, calculating a number of false positives and false negatives from the comparison, and choosing the sub-ranges at a point of minimized false positives, a point of minimized false negatives, and a point of best balance between false positives and false negatives.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
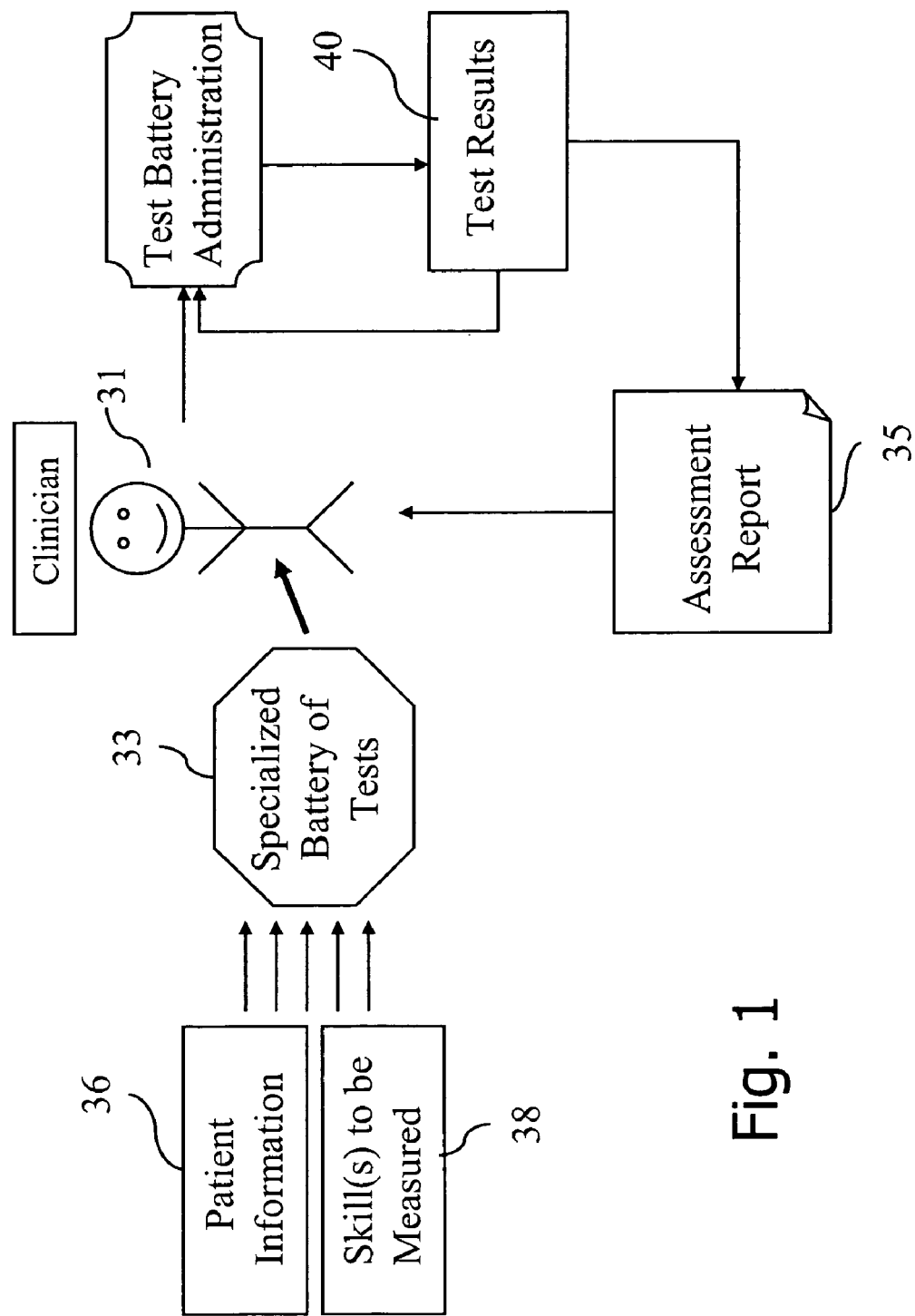
FIG. 1 is a diagrammatic overview of the basic elements of the method and system of the present invention according to one preferred embodiment.

The present invention is of a testing system and method for evaluation of neurological function. Specifically, the present invention can be used to differentiate between normal and pathological function for motor skills, logic, reasoning, coordination, verbal function, memory, and various other skills. In addition, it is designed to provide a package to a clinician, including a recommended battery of tests and a results report. The system and method described herein is designed to reduce bias due to the human nature of the tester, while still maintaining versatility, individualized attention and depth of analysis in testing.

The system and method of the present invention can be used across a wide range of performance levels—from normal individuals to those with extreme mental disabilities. There is a very wide range of tests, and various decision points, allowing a practitioner to closely monitor the performance of an individual, both at the time of the test and during follow up testing sessions. All of this can be done with relative ease due to the fact that the practitioner is provided with means for deciding what tests to administer and detailed, clear reports following each testing session. It is designed to be a practical, inexpensive medical tool that could be employed in the physician's office, in testing centers, or in the field and would provide reports in real time.

Before explaining at least one embodiment of the invention in detail, it is to be understood that the invention is not limited in its application to the details of construction and the arrangement of the components set forth in the following description or illustrated in the drawings. The general principles of the present invention will be described with reference to several embodiments, with specific details of several tests described fully. However, the invention is capable of other embodiments or of being practiced or carried out in various ways with many alternatives, modifications and variations, and many other tests may fall within the realm of the present invention. Accordingly, it is intended to embrace all such alternatives, modifications and variations that fall within the spirit and broad scope of the appended claims. Also, it is to be understood that the phraseology and terminology employed herein is for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

The principles and operation of a testing system and method according to the present invention may be better understood with reference to the drawings and accompanying descriptions.

Reference is now made to FIG. 1, which depicts a diagrammatic overview of the basic elements of the method and system of the present invention. As shown in FIG. 1, the basic elements revolve around a clinician 31 who is qualified to administer psychological tests and provide or direct a subject to appropriate medical care based on results of the test. The clinician 31 may be a physician, psychologist, neuropsychologist, social worker, or any other person who would perform a psychological or medical evaluation on an individual. The invention described herein is a system and method which provides the clinician 31 with the necessary tools for choosing and administering appropriate tests tailored for individual needs, as well as tools for receiving and interpreting the results of the administered tests. Thus, both a specialized battery of tests 33 and an assessment report 35 are provided to the clinician 31, before and after test administration, respectively. The specialized battery of tests 33 is compiled based on several factors including detailed patient information 36, and information about the cognitive skills 38 to be measured. Patient information 36 may include medical condition, age, presumed level of cognition, familiarity with the testing medium, and any other potentially relevant characteristics. Cognitive skills 38 may be very specific, such as memory, attention, or some other single characteristic, or may include a combination of several skills. In one embodiment, no prior presumption of cognitive level is provided and the specialized battery of tests 33 includes a general cognition testing battery. Once the specialized battery of tests 33 is compiled, it is sent to the clinician 31, who then administers the battery of tests 33 to a subject. The test results 40 are used to adjust the test itself while it is being administered. At the end of the testing session, the test results are compiled into an assessment report 35, which is easy to read and interpret.

The specialized battery of tests 33 is compiled based on patient information and information about which cognitive skills the clinician is interested in. Prior art systems have included testing some of these skills alone, or at most in linear combination with one or two other skills. The present invention allows for an expansion of the testing in order to provide a more complete picture of the subject's abilities and levels of performance. Thus, if the purpose of the testing session is to evaluate memory, a battery of memory tests will be provided, each one of which will test a different type of memory. If the purpose of the testing session is to evaluate general cognitive function, several different cognitive skills will be tested, such as memory, executive function, visual/spatial orientation, verbal function, attention, information processing, or any other cognitive skill which may be considered relevant. It should be readily apparent that any combination of tests may form a battery for various different evaluation purposes.

According to one embodiment, the clinician is provided with a testing wizard, which asks the clinician for specific details about the patient and the purpose of the test. The wizard then helps to determine the appropriate battery of tests based on the information provided by the clinician. According to an alternative embodiment, the clinician is provided with a list of battery names and a brief description of each one. In another embodiment, the battery of tests is automatically provided based on an initial testing segment to determine a performance level. In any case, the clinician is assisted in choosing an appropriate battery of tests. Additional details may be considered, including the order in which the different tests are administered, or the skill level at which the tests should be performed.

The decision-making tools used by the system to determine appropriate batteries of tests are based on published knowledge in the field of neuropsychology, and are taken from well-known sources, such as, for example, Spreen O & Strauss E: A Compendium of neuropsychological tests: Administration, norms, and commentary, NY: Oxford University Press (1991), Snyder, P. J. & Nussbaum, P. D. (Eds) *Clinical Neuropsychology*; and A Pocket Handbook for Assessment, American Psychological Association (1998). That is, an automated service provides a usable accumulation of knowledge gleaned from experts in the field, based on individualized parameters, similar to a consultation by a neuropsychologist.

An example of a chosen battery is a battery for a person displaying memory loss. If a physician wants to determine whether the memory loss is due to normal aging or might be due to the onset of a pathological condition, such as Alzheimer's, he would choose the mild cognitive impairment (MCI) scale, which focuses on issues that are important for that particular determination, such as memory and executive function. Another example would be a person with a mild head injury who is displaying poor concentration at work. In that particular case, a physician might choose a battery of tests including evaluation of attention, concentration, and short-term memory.

The tests themselves are designed to provide more information and more accurate information than prior art testing systems, while maintaining a distance from the test administrator so as to reduce human bias. Several unique concepts and features are present in many or all of the tests of the present invention. Some of these unique features are described hereinbelow. It should be noted that the discussion which follows is not intended to be presented in any particular order, and no significance should be placed on the order or the categorization of features discussed herein.

I. Subject/System Interface

All of the tests are designed with a simple and intuitive interface. Embodiments of the interface may include a computer monitor or other type of display in communication with a mouse, joystick, keyboard, number pad, touch screen, voice recognition system, or any other interface designed to provide communication between a user and a testing system. The use of this type of interface helps to eliminate any potential bias which may have been introduced based on unfamiliarity with the system or difficulty in executing the answers.

Additionally, although the instructions and interface are user-friendly, even for those with little or no previous experience, an optional orientation session is also provided, wherein very basic steps needed for performing the test are reviewed or taught. For example, if the test is given on a standard computer with a mouse and keypad, the basic features of the mouse and keypad are presented in an interactive manner so that the subject will not be limited in his/her performance by lack of previous experience. The orientation session may be particularly useful in testing the elderly, who may not be familiar with modern technological advances.

II. Practice Sessions

Once it is ascertained that the subject is familiar enough with the testing system to proceed without difficulty, it is then necessary to evaluate whether the test or battery of tests are appropriate for the individual. Built into each test is at least one practice session, which is used to determine several important facts. First, the practice session is used to evaluate the suitability of a test for a particular individual before beginning the scoring process. Generally, the subject is given certain simple instructions, and is provided with feedback so that he/she can learn the nature of the test, either with regard to the questions being asked or with regard to the mechanical performance of answering the questions, or with regard to any other basic element of the test. If a subject is not able to pass the practice portion of the test (according to predetermined criteria, such as accuracy), it is possible that the subject's cognitive ability falls outside of the range of suitability for the particular test and as such, the test is terminated and another test may be chosen.

Second, even for those individuals who do understand the basic instructions, there is often an initial learning period, which, if not accounted for, can skew the final scored results. By providing a practice session before each test, the learning period is primarily overcome during this time, wherein the subject is allowed to practice while being given feedback about his/her performance. In this way, the results can be expected to reflect the subject matter being tested, rather than a lack of familiarity with the test itself or other factors. Additionally, the level of the test can be adjusted to suit the subject based on the results of the practice session, as will be described in further detail hereinbelow with regard to the adaptive nature of the tests.

Finally, the practice session provides for a structured period where a test supervisor can interact with the subject to make sure everything is clear. Thus, the supervisor is able to completely avoid interaction with the subject during the actual test, thereby eliminating a further potential bias in the test results.

III. Adaptive Nature

Responses are dynamically analyzed on an ongoing basis both during the practice session and during the test itself. Thus, the level of difficulty can be adjusted to suit the particular individual.

In a first embodiment, the adaptive nature of the testing system includes a "dynamic floor/ceiling" feature for individual tests. This feature allows for the testing to be done at an appropriate level for each individual, or alternatively, to be terminated if the subject's performance is below a certain predetermined threshold, thereby providing more accurate results and data interpretation. The adaptive nature of the tests serves to eliminate static "ceiling" or "floor" effects. In a preferred embodiment, tests are designed to start at a low level of difficulty, and to build up to higher levels of difficulty as long as the subject continues to perform above a certain threshold. Preferably, groups of stimuli are presented at each level so that the score is based on more than one answer. When the subject is no longer able to perform above the threshold level, the test is terminated. In an alternative embodiment, tests are designed to start at a moderate level. Each question is then adjusted based on the previous answer. This convergence type of adaptive testing, although known in the field of questionnaire type testing, has not been previously used for performance type testing such as described in the present application.

In another embodiment, the adaptive nature of the testing system includes a track-based feature. Testing is begun at a moderate level so as to determine an optimal track. At least two tracks are available—one for a high performance level and one for a low performance level. In alternative embodiments, more than two tracks are available, with gradations of levels at each track. The initial moderate testing scheme includes several questions, the results of which are used to determine the appropriate track. This determination is made by, for example, using cut-off values for each track. The system then automatically switches to the determined track for the remainder of the testing session.

In yet another embodiment, the adaptive nature is expanded to include automatic battery presentation, wherein an initial testing scheme is used to determine which battery of tests is most appropriate. For example, for dementia there are available both a moderate battery of tests for the range of performance of normal through mild impairment and a separate battery of tests for the range of performance of moderate through severe impairment. An initial testing scheme would include a series of moderate questions of moderate difficulty, the results of which are used to determine the appropriate battery. This determination is made by, for example, using specific cut-off values for the initial set of questions of moderate difficulty. The system then automatically switches to the determined battery for the remainder of the testing session.

Thus, the subject is challenged according to his/her level and the level can be adjusted throughout so as to provide an optimal level of testing. This feature is also a useful tool for determination of a normal versus pathological level of function. By honing in on the most appropriate level of testing, it is possible for people to be tested within their functional category, rather than by comparing normal function to pathological function. Also, by grouping results from normal and pathological individuals, it is possible to obtain specific testing criteria for each of these groups. It should be noted that although specific levels of testing are described below with reference to each test, these levels are merely examples used to illustrate the concept of having several levels of testing within one testing session. A larger or smaller number of levels, as well as various types of levels based on speed, difficulty, or other criteria, are possible.

IV. Stimulus

The type of stimulus used for each particular test is designed so as to be most conducive to producing a response, without distractions or confusing information. Thus, the stimulus is designed in each case to be a simple indication of the task to be performed. Any confounding factors, such as extraneous visual information, are eliminated. Additionally, factors which may interfere with the subject's ability to understand or read the stimulus are avoided, such as language barriers, or letters which are too small.

Additionally, the choice of specific stimuli is made based on an assessment of appropriateness for individual tests. For example, tests involving scenes are not highly detailed, are realistic and are culturally independent. Alternatively, in tests in which the angle of a stimulus is important, the angle is chosen appropriately for the individual skill being tested. Generally, stimuli are chosen to most clearly isolate the skill being tested, without introducing extraneous complexities. Furthermore, the levels of complexity are predefined and are closely related to the choices of stimuli. Thus, what is presented on the monitor is designed to elicit relevant responses appropriate for the goals of each test. The general idea is to choose stimuli which measure the particular function, while minimizing all other influences. The limits of complexity and the choice of particular stimuli are based on published as well as tested psychological data for testing criteria. References for published data include, among others, Lu C H, Proctor R W: Influence of irrelevant information on human performance: effects of S-R association strength and relative timing in Quarterly Journal of Experimental Psychology, 54(1):95-136, and La Heij W, van der Heijden A H, and Plooij P: A paradoxical exposure-duration effect in the Stroop task: temporal segregation between stimulus attributes facilitates selection in Journal of Experimental Psychology: Human Perception and Performance, 27(3):622-32.

V. Quality Control

Certain features are incorporated into the system and into specific tests to ensure that the data are valid and that they are an accurate measure of the specific feature.

One important aspect of many of the tests is response time. In order to ensure accuracy of the timing mechanism within each individual's system, a built-in measurement mechanism is set to check the motherboard, thus revealing any potential discrepancies between the measured time and the actual time. This provides for accuracy in the 1-10 millisecond range, which is at least an order of magnitude more accurate than a typical Windows based program, for example. Results may then be adjusted to account for any discrepancies. In this way, an individual system which has little memory and thus is inefficient will not interfere with the results interpretation.

In addition to the above-mentioned quality control measures, final results are processed either on-line or off-line and are checked for missing data, and compared to an expected range of values to make sure that data analysis has been performed properly.

Figure 2:
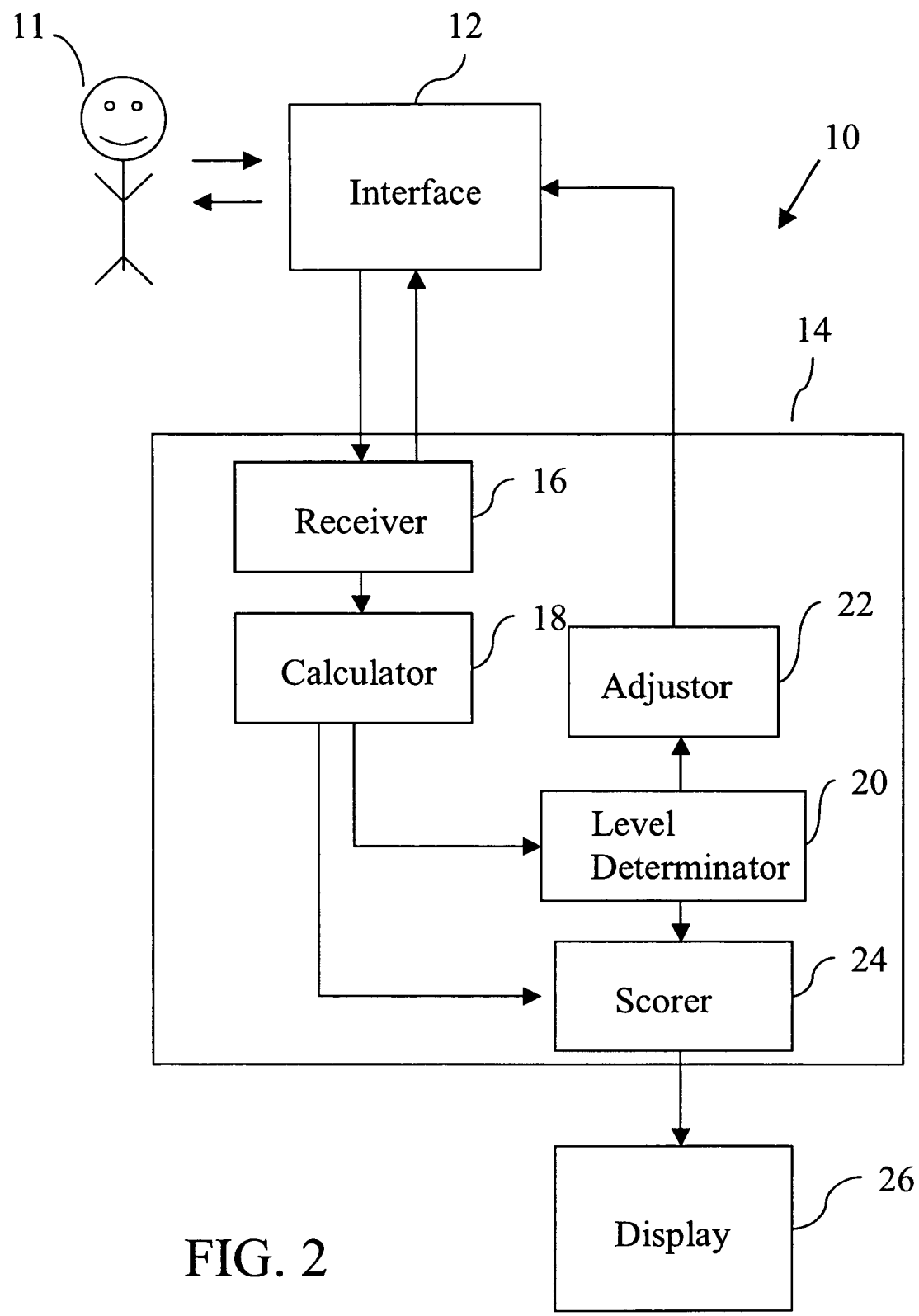
FIG. 2 is a block diagram illustration of a testing system according to a preferred embodiment of the present invention.

Reference is now made to FIG. 2, which is a block diagram illustration of a testing system 10 according to a preferred embodiment of the present invention. A subject 11 being tested is in communication with testing system 10 via an interface 12. Interface 12 is configured to accept data collected by responses of subject 11 to stimuli provided by testing system 10. Interface 12 communicates with system 10 via a processor 14, configured to accept and analyze the data, provide feedback to user 11, adjust the testing scheme, and send results. Processor 14 has a receiver 16 for receiving data, a calculator 18 for calculating performance, a level determinator 20, for determining a skill level of subject 11, an adjustor 22 for adjusting the level of testing, and a scorer 24 for determining a score based on the received data. The processor sends the processed score information to a display 26. Display 26 may be an audio or visual display, and is either directly or remotely connected to the rest of system 10.

Initially, a stimulus is presented to subject 11, who then responds to the stimulus. Both the presentation of the stimulus and the response thereto are directed through interface 12. In a preferred embodiment, interface 12 is a computer system having an input such as a mouse, keypad, joystick or any other input device, and a display for presentation of the stimulus. It should be readily apparent that any system useful for presentation of a stimulus and collection of responses may be used. However, it is preferable that interface 12 be intuitive and simple to understand. If necessary, an orientation session is provided so as to familiarize subject 11 with interface 12, thereby eliminating the possibility of bias due to lack of familiarity with the technology.

Receiver 16 collects responses from subject 11 through interface 12, and sends the data to a calculator 18. Calculator 18 calculates performance factors, such as accuracy, speed, etc., as will be described in further detail hereinbelow. General performance is rated based on certain predefined criteria, such as threshold levels, percentage of accurate responses, or any other criterion deemed to be relevant. Calculator 18 sends performance data to level determinator 20 and to scorer 24. Level determinator 20 determines an appropriate level of testing based on the performance data, and sends the data to both adjustor 22 and to scorer 24. Adjustor 22 adjusts the level of testing, which is directed through interface 12 to subject 11 for additional testing. In many instances, the determined level is also useful in calculating a final score. Scorer 24 uses data from level determinator 20 and from calculator 18 to determine a score. The score may be in the form of a number, a series of numbers, a chart or a graph or any other format. The score is sent to display 26 either via direct or remote connection, which then displays the score in an easily readable format.

It should be noted that level determinator 20 is helpful in determining both a level of testing for normal subjects, and whether the specific battery of tests is appropriate for subjects in a debilitated or diseased state. If it is determined that the specific tests being used are not appropriate for an individual, other tests with simplified stimuli and choices are used instead.

Examples of several specific tests are described herein. For clarity, the tests have been divided into categories relating to different cognitive functions. However, in many cases the tests overlap more than one category, as some of the tests are multifunctional in data collection and interpretation. The categories used herein are the following: motor skills, visual/spatial perception, memory, information processing, verbal function, and executive function. It should be readily apparent that although each test has specific unique features, many common features are shared between some or all of the tests, and each test described can be altered to serve various purposes. The purpose of the tests is both to evaluate an individual's ability as well as to help define parameters within which pathology can be defined.

A) Motor Skills:

Finger Tap Test

Figure 3:
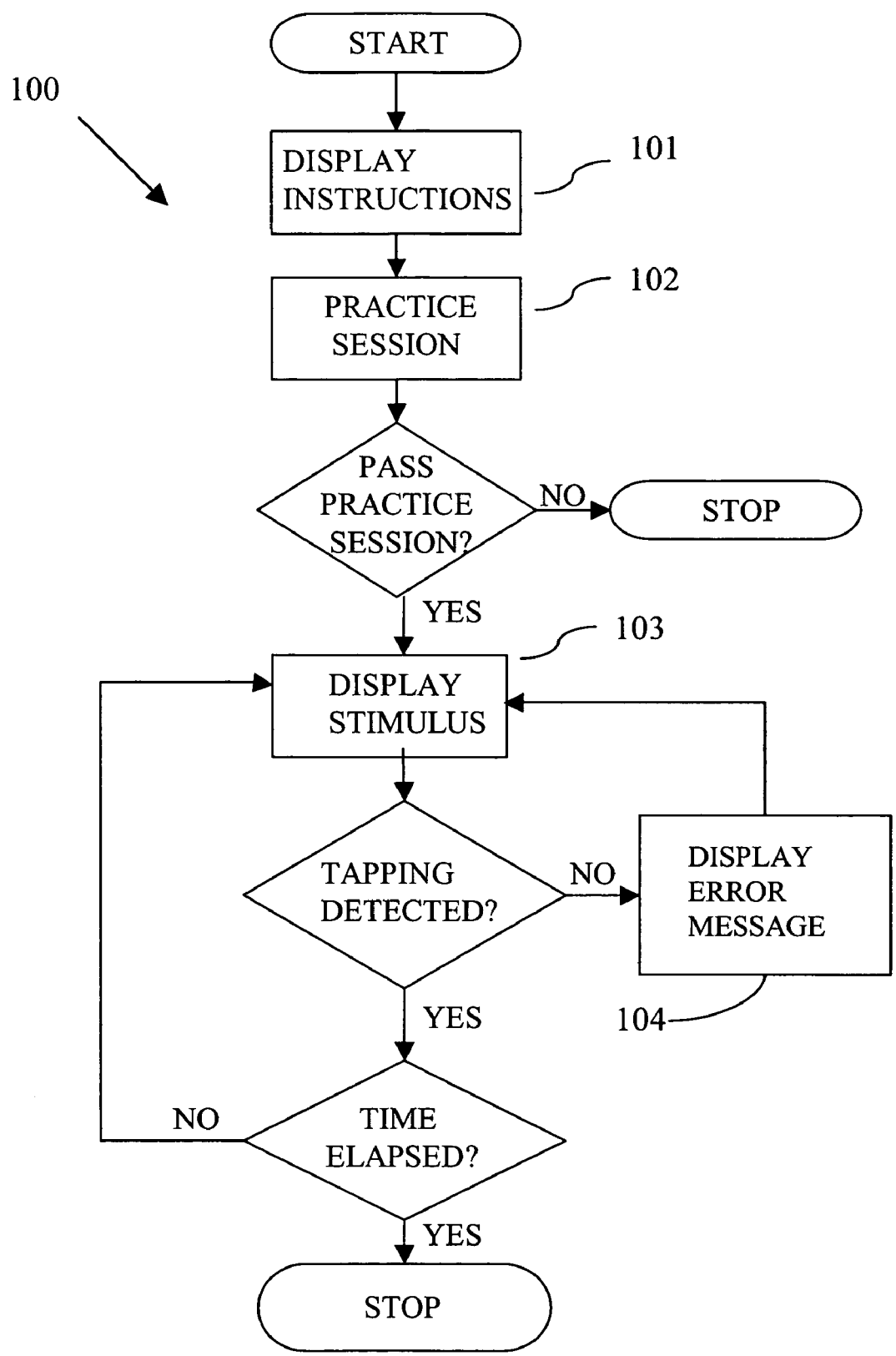
FIG. 3 is a flow diagram of the steps of a finger tap test according to one embodiment of the present invention.

FIG. 3 depicts a flow diagram of the steps of a finger tap test 100 according to one embodiment of the present invention. The purpose of this test is to assess speed of tapping, and regularity of finger movement.

At the beginning of the test, the system displays (step 101) instructions. The instructions describe what the subject will see on the screen, and instruct him/her what to do when the stimulus appears. The message may be very detailed, specifying, for example, which hand to use. The subject is asked to tap in response to a specific stimulus. Initially, the system runs a practice session (step 102), in which a very basic form of the test is given, along with feedback informing the subject whether or not the test is being done properly. The subject is given several chances to perform the requested task, and if the initial score is below a certain predetermined level, the test is terminated. In a preferred embodiment, the scoring is designed to elucidate whether or not tapping was detected. If it was detected a certain percentage of time, the test continues.

The main testing portion begins by displaying (step 103) a stimulus for a predetermined amount of time. In a preferred embodiment, the stimulus is a bar or line on the screen which increases in length with time. In alternative embodiments, the stimulus is a shape which moves across the screen, or is any other form and movement which is displayed for a predetermined amount of time. In one embodiment, the predetermined amount of time is 10-15 seconds. In a preferred embodiment, the stimulus is displayed for 12 seconds. It should be readily apparent that the stimulus may be displayed for any length of time which may be useful in testing the response. The subject is expected to repeatedly tap as quickly as possible in response to the stimulus, as explained in the instructions or by a test administrator prior to commencement of the testing portion. In a preferred embodiment, tapping is done on one of the mouse buttons. Alternative embodiments include tapping on a finger pad, a keypad, or any other button or object configured to receive proprioceptive information and convey the information to a processor.

If tapping is detected, data is collected during the time it takes for the stimulus to move across the screen, or until some other indication is made to stop. If tapping is not detected, the system displays (step 104) an error message, after which the stimulus is displayed again. The error message may be a reminder of how to respond. If tapping is detected, the test continues until the predetermined amount of time has elapsed. Once the time has elapsed, the test ends.

Detection of tapping is determined by specific criteria. For testing purposes, tapping is considered to not have occurred if the inter-tap interval, or ITI, is greater than a predetermined amount. In a preferred embodiment, the maximum ITI is 500 ms, but it should be readily apparent that any time span may be chosen.

Once the testing sequence is completed, outcome is determined based on several parameters, including the times at which the test began and at which the response was received, the overall mean and standard deviation of ITI for right hand and for left hand, and the number of taps per session.

Figure 4:
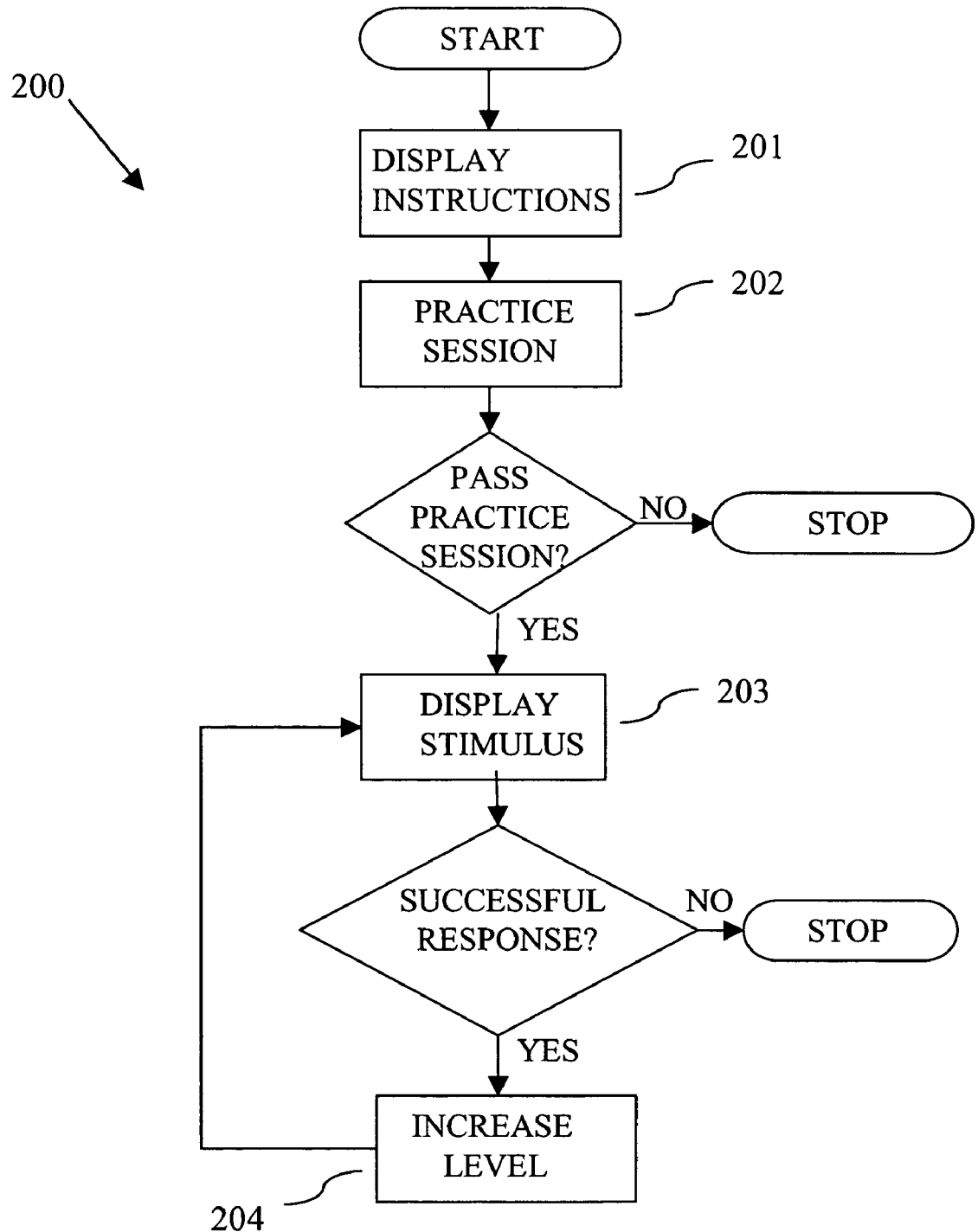
FIG. 4 is a flow diagram of the steps of a test according to one embodiment of the present invention.

Reference is made to FIG. 4, which depicts a general flow diagram representation of tests that have more than one level. Thus, the descriptions of the tests that follow will be more easily understood in conjunction with FIG. 4.

Catch Test

Figure 5:
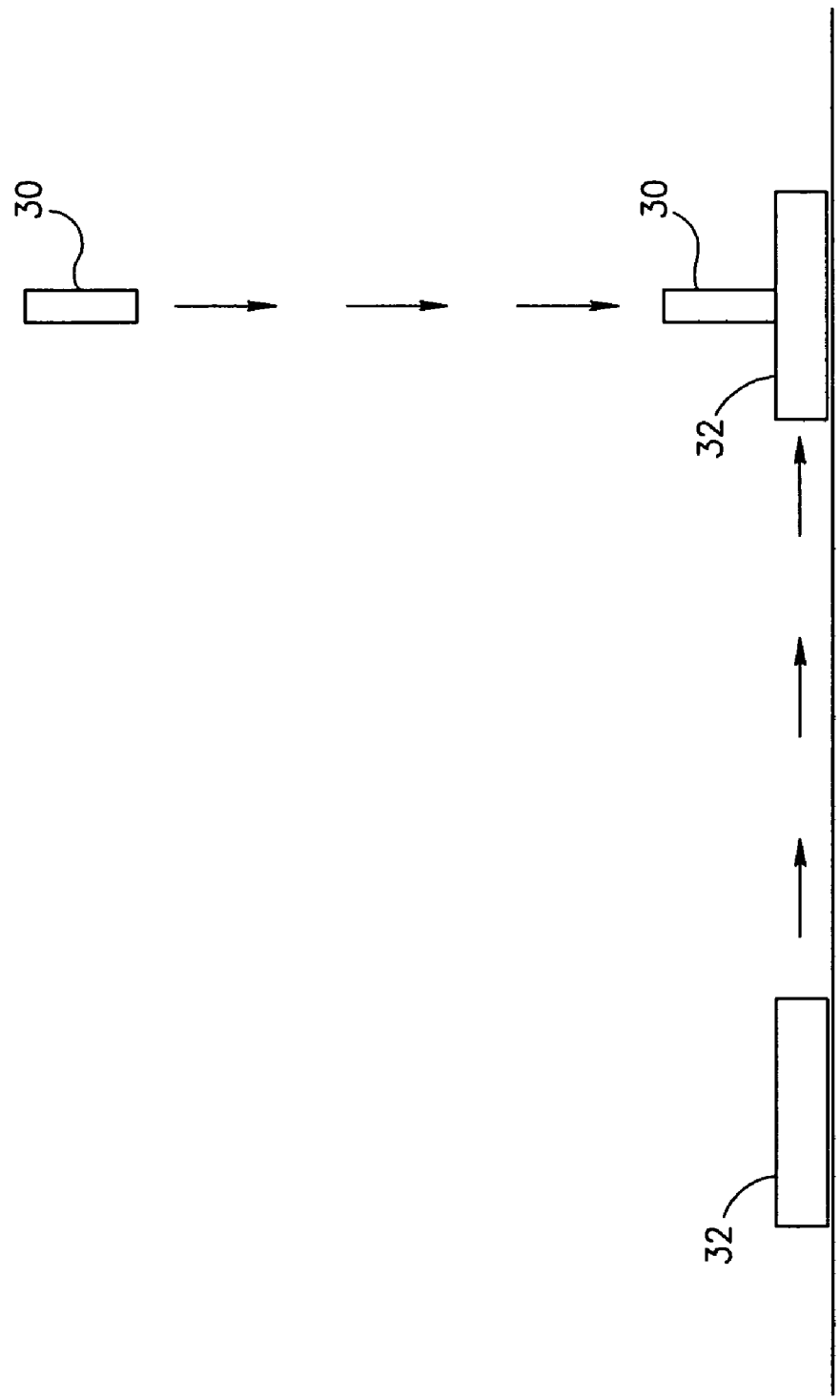
FIG. 5 is a sample screen shot of a catch test according to one embodiment of the present invention.

Reference is made to FIGS. 4 and 5, which depict a flow diagram of the steps of a test 200, and a sample screen shot of a catch test in session, according to one embodiment of the present invention. The purpose of this test is to assess motor related reaction time, hand/eye coordination, motor learning and planning, performance speed, and spatial perception. The subject is asked to catch a first object 30 falling from the top of a screen using a second object 32 on the bottom of the screen, as shown in FIG. 5 and described in further detail hereinbelow. An important aspect of this test is that its simplicity allows for a very short learning curve, thereby minimizing effects of prior computer use on test performance. That is, a person with little or no experience is able to perform comparably with a person with a great deal of computer experience within a very short time, thereby allowing for isolation of the particular skills to be tested.

First, the system displays (step 201) a set of instructions. The instructions direct the subject to catch the falling object with a movable object on the bottom of the screen. In a preferred embodiment, the falling object 30 is a simple shape and color, such as a green square or a blue ball. In a preferred embodiment, the movable object 32 is a straight line or some other simple shape that might represent a paddle or racquet, such as the shape depicted in FIG. 5. It should be readily apparent that any suitable shape may be used. In a preferred embodiment, movable object 32 is a long rectangular shape of 10-20 mm×1-5 mm. In an exemplary preferred embodiment, movable object 32 is 15×2 mm. In the instructions, the subject is directed as to how to move object 32 from side to side. Any button may be configured to allow object 32 to move in a controlled manner. In a preferred embodiment, the right mouse button may be used to move object 32 to the right and the left mouse button to move object 32 to the left, or arrow buttons on a keyboard may be used. In a preferred embodiment, each mouse click moves the object one length, and the object cannot leave the bounds of the screen. However, it should be readily apparent that the control mechanism is not limited to those listed herein, and any suitable control mechanism may be used.

The test begins by providing (step 202) a practice session. In the practice session, the subject is expected to catch a falling object. If the subject catches the object, the system displays a positive feedback message. If the subject does not catch the element, the system displays a feedback message explaining that the objective is to catch the object falling from the top of the screen, and further explaining how to move the object. Once a predetermined number of trials are successfully completed, the test moves on to the next level. Successful completion of the practice session is determined by a percentage of successful catching of the object. In a preferred embodiment, the subject must catch the object at least 2 out of 3 times in order for the testing session to continue.

If the practice session is passed, the test continues by displaying (step 203) the falling object 30 at a predetermined speed and calculating the number of successful catches. If the catching score is higher than a predetermined level, the test continues by moving onto the next level, at which object 30 is configured to fall at a faster speed. If the catching score is lower than the predetermined level, the testing session is terminated.

In a preferred embodiment, in the first level of testing it takes between 3000 and 5000 ms for object 30 to reach the bottom of the screen. In an exemplary preferred embodiment, in the first level of testing it takes 4000 ms for object 30 to reach the bottom of the screen. Subsequent levels each have a faster falling rate than the previous level. Thus, in a preferred embodiment, at the second level of testing it takes 3000 ms for the element to fall, at the third level it takes 2000 ms and at the fourth level it takes 1000 ms. It should be readily apparent that any time interval may be used, as long as each level has a faster rate than the previous one. In addition, any number of levels may be used, until the subject reaches a point at which the test is too difficult.

The starting position of both the falling object 30 and the movable object 32 in relation to the falling element vary from trial to trial. In addition, the path of falling object 30 is also variable, and may be useful in increasing the difficulty of the test. For all levels, if the subject performs a successful catch a predetermined number of times, the test moves on to the next level. Otherwise, the test is terminated.

The system collects data related to the responses, including timing, initial location of element and object, number of errors, number of moves to the left and to the right, and level of testing, and presents a score or multiple scores based on the above parameters.

B) Visual/Spatial Perception:

3-D Spatial Orientation Test

Figure 6:
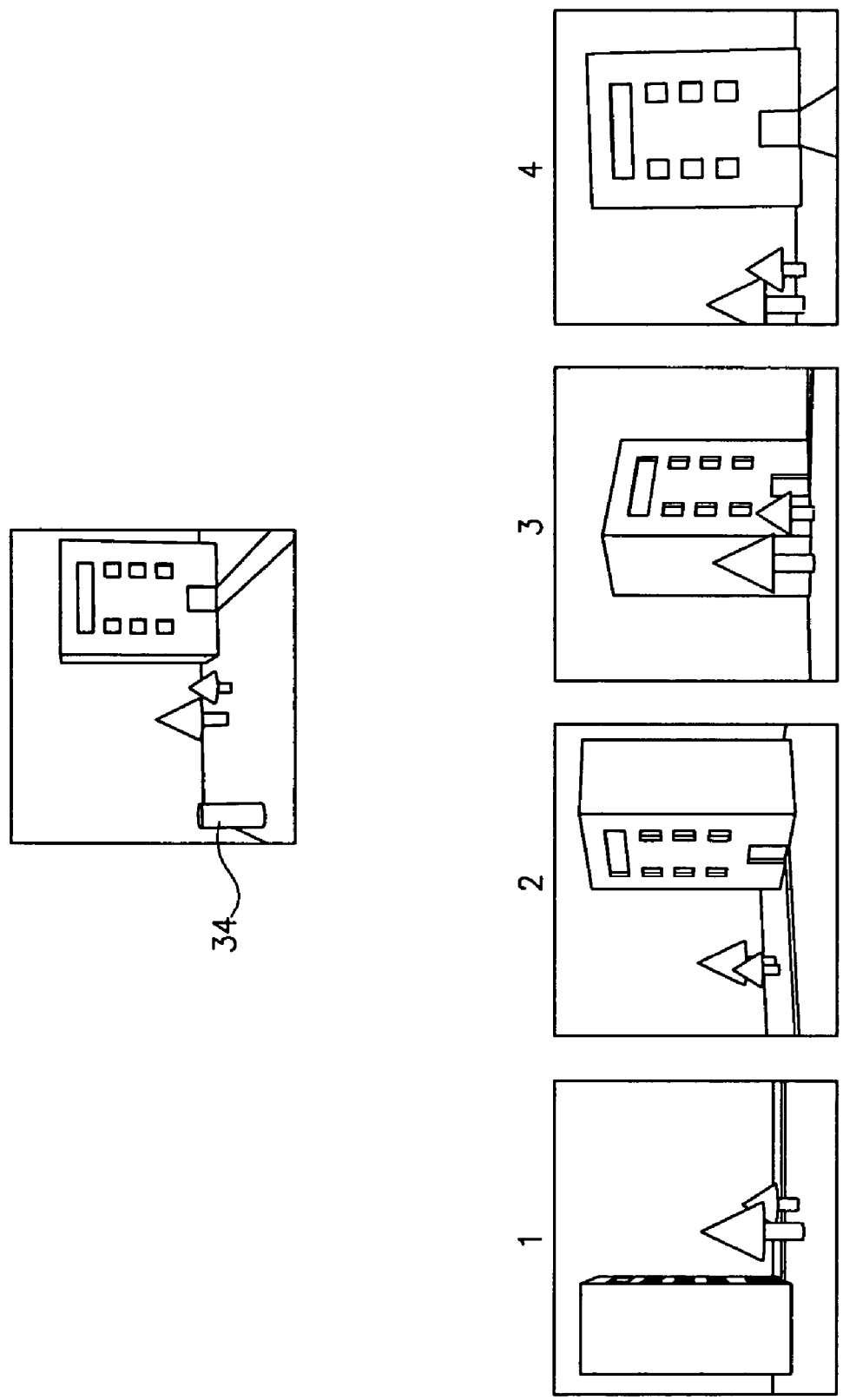
FIG. 6 is a sample three-dimensional picture shown in a 3-D spatial orientation test, in accordance with one embodiment of the present invention.

A 3-D spatial orientation test is provided, according to one embodiment of the present invention. The purpose of this test is to assess spatial perception and mental rotation capabilities. FIG. 6 depicts a sample three-dimensional picture shown in the 3-D spatial orientation test.

At the beginning of each test, a three-dimensional picture such as the one shown in FIG. 6 appears on a screen with a marker 34 located in variable places on the picture. The marker 34 is of a specified shape or color, for example, a blue line, a green diamond, a red pillar or any other suitable form. A set of pictures is shown on another part of the screen. Each of the pictures represents a potential view of the picture as seen from the position of marker 34. The subject is expected to choose the most correct view, based on the pictures shown on the screen. Neither the picture nor the marker is limited to the ones described and shown herein, but rather, may be any three-dimensional orientation of objects suitable for testing spatial orientation. It should be noted, however, that the choice of scene is predetermined based on simplicity and least likelihood of causing interference with the actual skills being tested.

The test may include several levels and as such, the basic format is shown FIG. 4. First, the system displays (step 201) a set of instructions. The instructions direct the subject to imagine standing at the place of the marker 34, and to visualize what view of the three-dimensional picture would be seen from that position. In a preferred embodiment, an example is displayed, followed by the correct answer for further edification. The instructions end with an explanation of how to choose the correct answer, for example, by pressing the correct number on the number pad of a keyboard.

The test begins (step 202) with a practice session. During the practice session, the choices remain on the screen until one of the displayed pictures is selected as a response, and once a selection is made, positive or negative feedback is provided to the subject. For the practice session, the marker is placed directly in front of the scene or in some other similarly easy to visualize location. Once a predetermined number of trials are successfully completed, the regular testing session is administered. A determination of whether or not the practice session was successfully completed is made based on the number of correct responses. In one embodiment, if two answers are sequentially correct, the test practice session has been completed successfully. If not, two additional pictures are shown. If the overall accuracy is two out of four correct or less, the test is terminated. Otherwise, the test moves on to the next level. It should be readily apparent that the required number of correct responses can be varied.

Once the practice session is completed, the testing round begins. The system displays (step 203) a picture similar to the one displayed in the practice session. In a preferred embodiment, the marker 34 is placed in a slightly more difficult location, such as on one side or at varying distances. In one embodiment, a sample size of at least 10-20 pictures is collected. For all levels of the testing round, no feedback is given to the subject. The accuracy is then calculated. If the performance is acceptable based on predetermined criteria, the testing session moves (step 204) onto the next level. Otherwise, the test is terminated. In one embodiment, an acceptable criterion is at least 70% accuracy.

A higher level tests relative spatial perception. A first picture is shown on one part of a screen, and four choices are shown on a different part of the screen, as in the other levels. However, although all four of the choices show pictures similar to the first one at various angles, only one of the four options actually has the same elements in the same relative locations. Thus, the subject is required to determine not only what the approximate view would be from the marker, but also which view is an accurate depiction of the original scene at a different angle. It should be readily apparent that any number of levels of increasing difficulty may be used.

The system collects data related to the responses, including timing, correctness and level of testing, and presents a score based on the above parameters.

C) Memory:

Verbal Memory Test

A verbal memory test is provided, whose purpose is to evaluate a subject's ability to remember pairs of words that are not necessarily associated with one another. Reference is again made to FIG. 4, which is a flow chart depiction of the basic steps of a test in accordance with an embodiment of the present invention. At the beginning of the test, the system displays (step 201) a set of instructions explaining that he/she will be shown pairs of words to remember, and that at least some of the words do not normally go together.

The test begins (step 202) with a practice session. Within the practice session as well as the testing sessions described below, there are two portions to the test. The first part of the test is the preparatory phase, in which the system displays a specified number of word pairs for a particular amount of time, with a pause in between each display. In a preferred embodiment, the practice session includes three word pairs, each of which is displayed on the screen for 2500 ms with a 200 ms pause in between. The second part of the test is the quiz phase, in which the system displays the first word of the first pair, and four choices, one of which is the second word of the first pair. The other three are decoys, some of which are specifically related to one of the words of the pair. The screen remains visible until there is a response. This is repeated for the second word pair and again for the third, until the total number of word pairs has been tested. During the practice session, the system provides positive and negative feedback to the subject after each response. If the subject passes a predetermined threshold (such as ⅔ correct, for example), the test moves on to the next level. Otherwise, it repeats the practice level one time, and if the threshold is still not reached, the test is terminated.

At the testing level, word pairs are displayed (step 203). More pairs of words are shown than in the practice session, and no feedback is given. A specified number of word pairs are shown, and if the responses are not 100% correct, the test is repeated by showing all of the word pairs again and asking the subject to choose the correct response. Repetitions can occur up to a specified number of times. In a preferred embodiment, repetitions may occur up to six times. If the accuracy is less than, for example, 30% on two subsequent repetitions, the test is terminated. If the accuracy is higher than that amount, the test moves on to the next level. Higher levels may include more difficult pairs, more pairs, and shorter intervals.

In order to study delayed recognition, this test may be retrieved at a later time within the battery of tests in order to see whether the subject remembers the pairs that were shown at the beginning. For example, this test may be given, then the subject will be tested on motor skills or some other testing scheme, and then this test will return, without showing the individual the original word pairs again. Certain factors may be relevant, including the sequence of tests and the time interval between when the original pairs were shown and when the subject is asked to retrieve it again from his/her memory.

The system collects data related to the responses, including the number of repetitions, the level, the accuracy and correctness of the responses, a slope of learning across the repetitions, and accuracy of the delayed recognition test, and determines a score based on these parameters.

Non-Verbal Memory Test

There is provided, in accordance with another embodiment of the present invention, a non-verbal memory test. The purpose of the test is to evaluate a subject's ability to remember the spatial orientation of a picture. Thus, this test is a spatial perception test as well as one of memory. At the beginning of the test, the system presents (step 201) a set of instructions. The test begins (step 202) with a practice session. The first part of the test is the preparatory phase, in which the system displays a specified number of images, one at a time for a particular amount of time, with a pause in between each display. In a preferred embodiment, the practice session includes one image, which is displayed on the screen for 5 seconds. The second part of the test is the quiz phase, in which the system displays four choices, one of which is the image that was shown 20 seconds earlier. The other three are decoys, some of which are specifically related to the image or its orientation. The screen remains visible until there is a response. During the practice session, the system provides positive and negative feedback to the subject after each response. If the subject passes a predetermined threshold (such as ⅔ correct), the test moves on to the next level. Otherwise, it repeats the practice level one time, and if the threshold is still not reached, the test is terminated.

Figure 7:
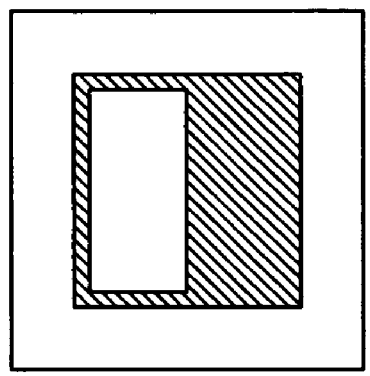
FIG. 7 is a screen shot of images shown in the preparatory phase of a non-verbal memory test.
Figure 7:
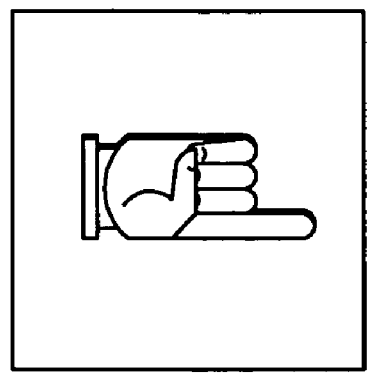
Figure 7:
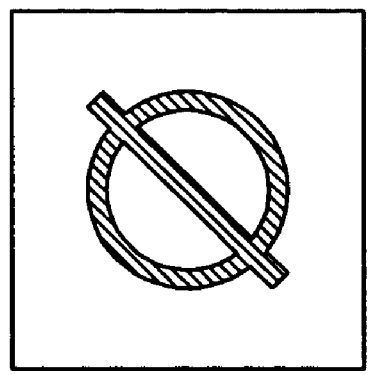
Figure 7:
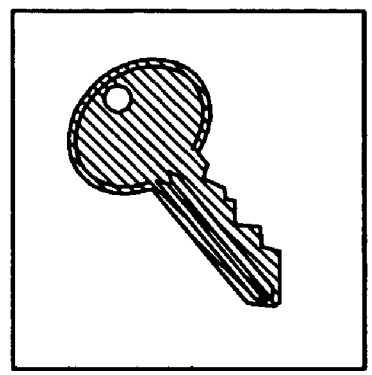
Figure 7:
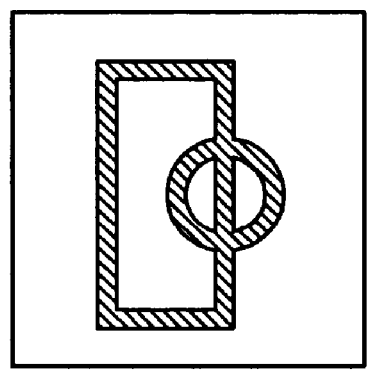
Figure 7:
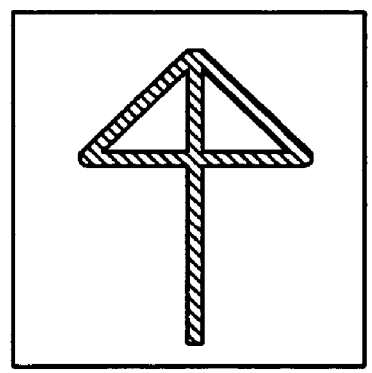
Figure 7:
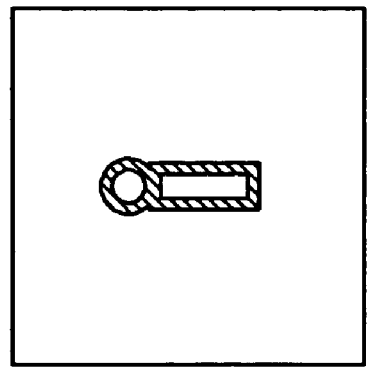
Figure 7:
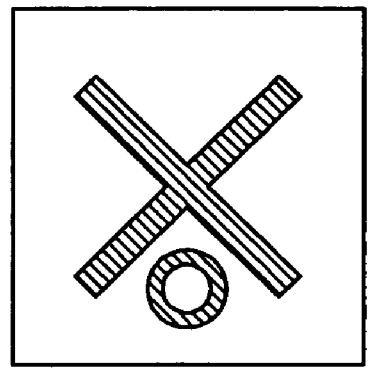
Figure 8:
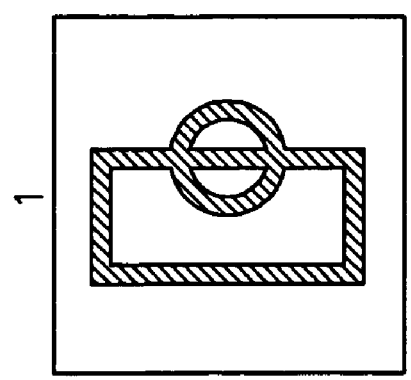
FIG. 8 is a screen shot of images shown in the quiz phase of the non-verbal memory test of FIG. 7.
Figure 8:
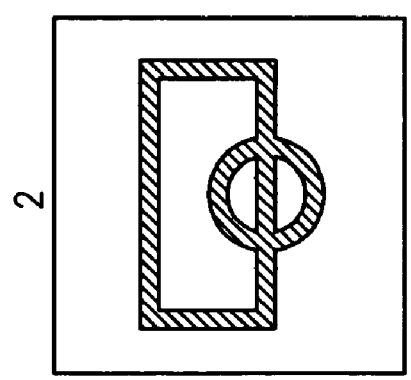
Figure 8:
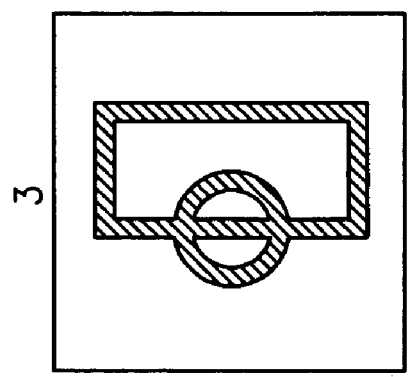
Figure 8:
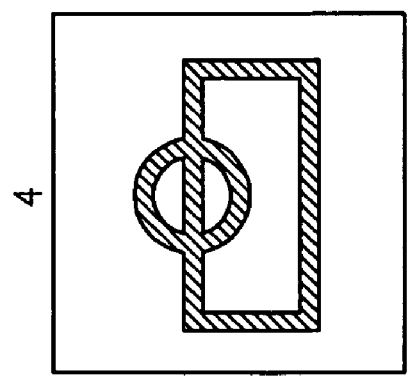

Reference is now made to FIGS. 7 and 8, which are examples of screen shots of images shown in the preparatory phase and the quiz phase of the test. It should be readily apparent that the images are not limited to the ones shown herein, but rather, any suitable images may be used. As shown in FIG. 7, during the preparatory phase, several images are shown together for 20 seconds. During the quiz phase, one of the images from the screen shot of FIG. 7 is shown in several possible orientations, such as is depicted in FIG. 8. The subject is asked to choose the correct orientation. In a preferred embodiment, eight images are shown in the preparatory phase, and if the responses are not 100% correct, the test is repeated. Repetitions can occur up to a predetermined number of times, preferably six. If the accuracy is less than a predetermined amount on two subsequent repetitions, the test is terminated. In a preferred embodiment, the predetermined amount is 30%. A delayed memory test may be performed later within the testing series to see whether the individual remembers the orientations shown previously, similarly to the delayed pair verbal test described above.

The system collects data related to the responses, including the number of repetitions, the level, the accuracy and correctness of the responses, a slope of learning across the repetitions, and accuracy of the delayed recognition test, and determines a score based on these parameters.

D) Information Processing:

Staged Math Test

A staged math test is provided in accordance with one embodiment of the present invention. The purpose of the test is to evaluate a subject's ability to process information, testing both reaction time and accuracy. Additionally, this test evaluates math ability, attention, and mental flexibility, while controlling for motor ability. The test is administered at increasing levels of complexity.

In a preferred embodiment, the test includes at least three basic levels of difficulty, each of which is subdivided into subsection levels of speed. The test begins with a display of instructions (step 201) and a practice session (step 202). The first subsection level of the first level is a practice session, to familiarize the subject with the appropriate buttons to press when a particular number is given. For example, the subject is told that if the number is 4 or less, he/she should press the left mouse button. If the number is higher than 4, he/she should press the right mouse button. The instructions continue with more detailed explanation, explaining that if the number is 4, the subject should press the left mouse button and if the number is 5, the subject should press the right mouse button. It should be readily apparent that any number can be used, and as such, the description herein is by way of example only.

A number is then shown on the screen. If the subject presses the correct mouse button, the system responds positively to let the user know that the correct method is being used. If the user presses an incorrect mouse button, the system provides feedback explaining the rules again. This level continues for a predetermined number of trials (5 in a preferred embodiment), after which the system evaluates performance. If, for example, 4 out of 5 answers are correct, the system moves on to the next level. If less than that number is correct, the practice level is repeated, and then reevaluated. If after two practice sessions the performance level is still less than 80%, the test is terminated.

The test is then performed at various levels, in which a stimulus is displayed (step 203), responses are evaluated, and the test is either terminated or the level is increased (step 204). The next three subsection levels perform the same quiz as the trial session, but at increasing speeds and without feedback to the subject. The speed of testing is increased as the levels increase by decreasing the length of time that the stimulus is provided. Thus, in a preferred embodiment, the first set of stimuli are provided for 1500-2500 ms each, the next set for 750-1500 ms each and the final set for 0-750 ms each. In all three subsection levels, the duration between stimuli remains the same (1000 ms in a preferred embodiment).

The next level of testing involves solving an arithmetic problem. The subject is told to solve the problem as quickly as possible, and to press the appropriate mouse button based on the answer to the arithmetic problem. For the example described above, if the answer to the problem is 4 or less, the subject must press the left mouse button, while if the answer to the problem is greater than 4, the subject must press the right mouse button. The arithmetic problem is a simple addition or subtraction of single digits. As before, each set of stimuli is shown for a certain amount of time at the first subsection level and subsequently decreased (thus increasing speed of reaction time) at each further level. In a preferred embodiment, three levels of speed are used, wherein the stimulus is shown for 1500-2500 ms, 750-1500 ms and 0-750 ms respectively. A minimum of 10 stimuli is provided for each level.

The third level of testing is similar to the second level, but with a more complicated arithmetic problem. For example, two operators and three digits may be used. After each level of testing, accuracy is evaluated. If accuracy is less than 70% at any level, then that portion of the test is terminated. It may be readily understood that additional levels are possible, both in terms of difficulty of the arithmetic problem and in terms of speed of response.

It should be noted that the mathematical problems are designed to be simple and relatively uniform in the dimension of complexity. The simplicity is required so that the test scores are not highly influenced by general mathematical ability. The stimuli are also designed to be in large font, so that the test scores are not highly influenced by visual acuity. In addition, since each level also has various speeds, the test has an automatic control for motor ability.

The system collects data regarding the response times and their associated variances, accuracy and level reached, and accuracy divided by reaction time, and calculates scores based on the collected data.

E) Verbal Function:

Verbal Naming and Rhyming Test

A verbal naming and rhyming test is provided to evaluate a subject's verbal function. It is made more difficult by the use of semantic foils, requiring an executive function (frontal lobes of the brain) to suppress the natural tendency towards the semantic foil, favoring the phonological choice.

The first level is a practice/explanation level, in which the system explains (step 201) to the subject that the object of the test is to choose the word that rhymes with a picture shown on the screen. Examples of pictures with rhyming words are shown. Next, the system displays a picture on the screen for a predetermined amount of time (1000 ms in a preferred embodiment), and two choices of words are displayed: one which rhymes with the picture and one which is semantically related to the picture. The subject must choose the word that rhymes as quickly as possible by pressing the corresponding number on the number pad. Feedback is provided if the answer is incorrect. If accuracy is ⅔ or higher, the test moves on to the next level. Otherwise, the practice session is repeated. If accuracy is still less than ⅔, the test is terminated. Thresholds for terminating or continuing tests are variable and are not limited to those described herein.

For the testing levels, the subject is asked to choose the word that rhymes, as in the practice session, but without feedback. Several levels of testing may be performed, each of which is more difficult in terms of the stimulus. The level of difficulty may be related to the subject's familiarity with the name of the stimulus. It should be noted that cultural and language differences are important for this test. This test may be available in various languages, and for different cultural groups.

The system measures response time, accuracy, and level and computes a score based on the measured parameters.

Naming Test

The naming test is a subtest of the rhyming test, which serves two purposes. First, it tests different verbal skills than the rhyming test, and secondly, it is a control for cultural bias. Thus, a response which was wrong both on the rhyming and on the naming test, would be discounted for the rhyming test. In this way, a picture either unrecognized or referred to by a different name would not count in the final scoring. Preferably, the naming test is performed after the verbal test so as not to interfere with the thought process involved in figuring out rhyming words versus related words. At each level, if accuracy is less than, for example, 70%, the test is terminated. Thus, the overall language tests provide sensitivity to multiple stages of verbal fluency impairment.

F) Executive Function:

The following series of tests are designed to test higher brain function, such as reasoning, etc. Some of them have dual or triple purposes as well, as will be described further hereinbelow.

Stroop Test

A stroop test is a well-known test designed to test higher brain functioning. Specifically, this test measures the facility with which an individual can shift his perceptual set to conform to changing demands and suppress a habitual response in favor of an unusual one. In this type of test, a subject is required to distinguish between two aspects of a stimulus. In the stroop test described herein, the subject is shown words having the meaning of specific colors written in colors other than the ones indicated by the meaning of the words. For example, the word RED is written in blue. The subject is required to distinguish between the two aspects of the stimulus by selecting a colored box either according to the meaning of the word or according to the color the word is written in. The additional parameter of speed is measured simultaneously.

The first part of the test is a practice session. The system displays two colored boxes and asks the subject to select one of them, identifying it by color. Selection of the appropriate box may be accomplished by clicking the right or left mouse button, or by any other suitable method. The boxes remain visible until a selection is made. After responding, the system provides feedback if the incorrect answer was chosen. The practice session is repeated several times. If the performance is less than 80%, the practice session is repeated. If it is still less than 80% after another trial, then the test is terminated.

Once the practice session is completed, the system presents a random word written in a certain color. In addition, the system presents two boxes, one of which is the same color as the word. The subject is required to select the box corresponding to the color of the word. No feedback is given. This test is repeated several times, preferably 10. On the next level, the system presents the words "GREEN", "BLUE" or "RED", or another word representing a color. The word is presented in white font, and the system concurrently presents two boxes, one of which is colored corresponding to the word. The subject is required to select the box corresponding to the color related to the meaning of the word. No feedback is given. This test is repeated several times, preferably 30 times, or at least 2-3 times the number of samples as the first part. In this way, the subject gets used to this particular activity.

The next level is another practice session, in which the system presents a color word written in a color other than the one represented by the meaning of the word. The subject is instructed to respond to the color in which the word is written. Because it is a practice session, there is feedback. The test is repeated several times, and if the performance is not above a certain level, the test is terminated. If the subject is successful in choosing the color that the word is written in rather than the color that represents the meaning of the word, the next level is introduced.

An additional level includes presentation of a word in white that names a color. The subject is instructed to choose the square which is the color named by the word.

The final level is the actual "stroop" test, in which the system displays a color word written in a color other than the one represented by the word. The word is visible together with two options, one of which represents the color the word is written is. The subject is required to choose that option. This test is repeated numerous times (30 is optimal), and there is no feedback given. Level, accuracy and response time and its associated variance, are all collected and analyzed.

Go/NoGo Response Inhibition

A Go/No Go Response Inhibition test is provided in accordance with one embodiment of the present invention.

The purpose of the test is to evaluate concentration, attention span, reaction time, and the ability to suppress inappropriate responses.

The first level is a practice session. The system displays a colored object, such as a box or some other shape. The object is a single color, preferably red, white, blue or green. It should be noted that by using a color as a stimulus, rather than a word such as is the case in prior art tests of this type, the test is simplified. This simplification allows for subjects on many different functional levels to be tested, and minimizes the effect of reading ability or vision. The subject is required to quickly select a mouse button for the presence of a particular color or not press the button for a different color. For example, if the object is blue, white or green, the subject should quickly press the button, and if the object is red, the subject should refrain from pressing the button. It should be readily apparent that any combination of colors may be used.

The first level of the test is a practice session, wherein the subject is asked to either react or withhold a reaction based on a stimulus. Each stimulus remains visible for a predetermined amount of time, and the subject is considered to be reactive if the response is made before the stimulus is withdrawn. In a preferred embodiment, the object remains visible for 400 ms. In a preferred embodiment, the system presents two red objects and two different colored objects, one at a time, each for approximately 400 ms. The subject is asked to quickly press any mouse button when any color other than red is displayed, and to not press any button when a red color is displayed. Feedback is provided in between each of the trials to allow the user to know whether he/she is performing correctly. If the subject has at least ¾ correct, he/she moves on to the next level. Otherwise, he/she is given one more chance at a practice round, after which the test continues or is terminated, depending on the subject's performance.

There is only one testing level for this particular embodiment, in which the stimuli are similar to the ones given in the practice session, but the subject is not provided with any feedback. Both sensitivity and specificity are calculated. Outcome parameters include accuracy, reaction time and its associated variance, a composite score computed as accuracy divided by reaction time, number of errors of omission, number of errors of commission, and reaction time associated with errors of commission.

Non-Verbal IQ Test

A Non-verbal IQ Test (or Problem Solving Test) is provided in accordance with one embodiment of the present invention. The purpose of the test is to evaluate non-verbal intelligence, particularly logic and reasoning skills. The subject is required to choose the best match of a set pattern, and the test has increasing levels of difficulty.

The first level of the test is a practice session, in which the subject is shown one set of four picture words, with one picture missing. Several choices appear, wherein one of the choices is the missing picture and the others are decoys specific to each test. In level one, all four picture words are identical, and the correct picture simply has to be chosen. Feedback is provided if the response is incorrect.

Figure 9:
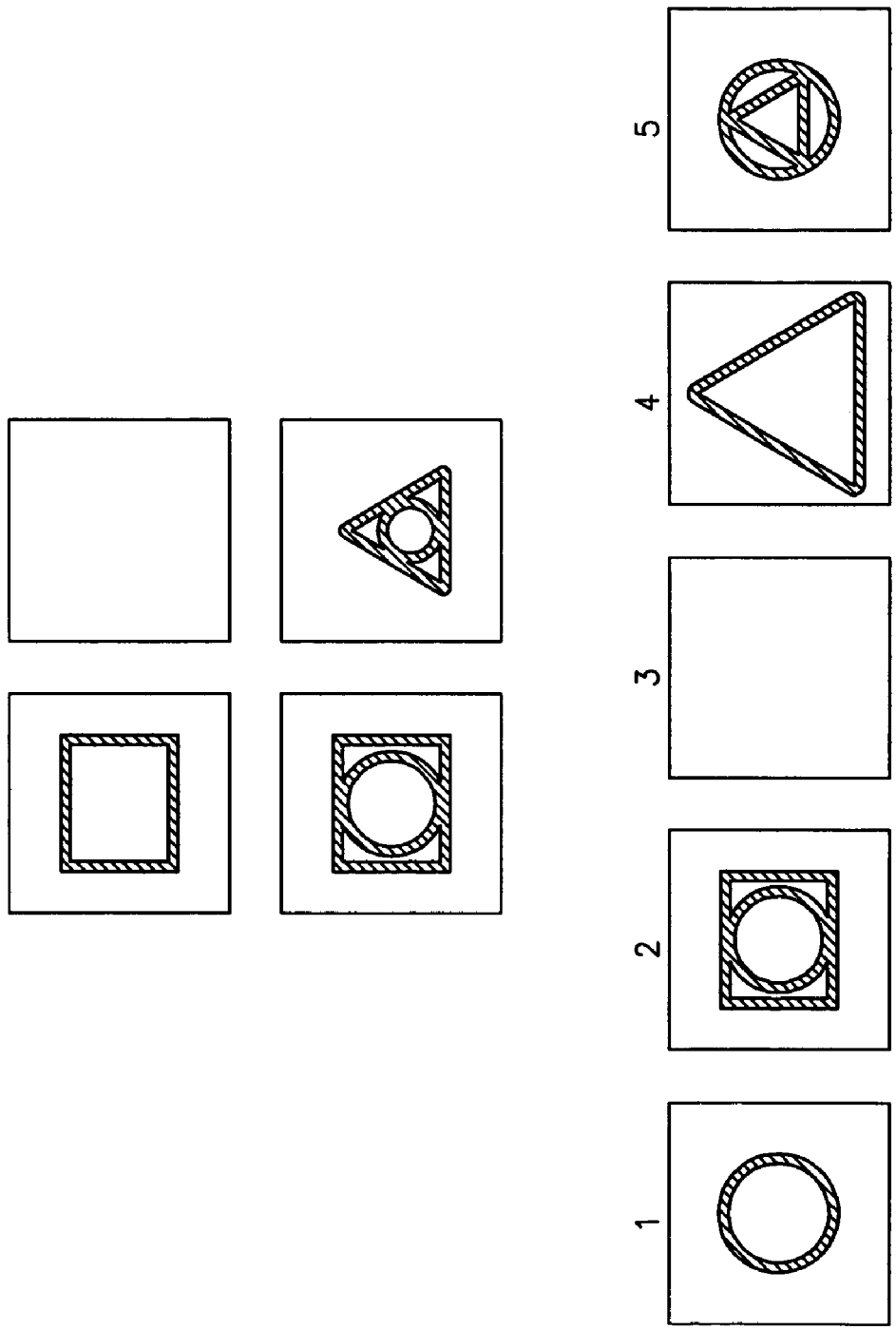
FIG. 9 is a screen shot of images shown in a non-verbal IQ test.

Reference is now made to FIG. 9, which shows a screen shot of an example of a stimulus and a set of choices for the test described herein, according to one embodiment. As shown in FIG. 9, three shapes are shown, and they form a particular pattern, with one form missing. The subject is required to choose the best match from the choices shown on the bottom of the screen. The subject has to use logic skills in order to arrive at the correct answer. The levels of the sets become increasingly more difficult. The accuracy, the level of testing and the response time are all measured and compiled into final scores. The outcome parameter includes a total accuracy score that incorporates performance at different levels of difficulty.

VI. Data Processing

Testing data are organized into an assessment report, which is then sent to the clinician. Data are processed and compiled in a way which gives the clinician an overview of the results at a glance, while simultaneously including a large amount of information. Data are accumulated and compiled from the various tests within a testing battery, resulting in a composite score. A report showing results of individual parameters, as well as composite scores is then generated.

There are several levels of processing the data, as follows:

1. Raw performance measures are generated for each test based on accuracy, response time, level, or specific combinations or composite scores of the measured parameters. Raw data include information about stimulus type, onset and offset of the stimulus (in milliseconds, for example), expected response type, actual response type, and time of response. An accuracy score and a response time score are computed for each trial. In one embodiment, accuracy is averaged for each level and is calculated as the total number of correct responses per total number of trials. Response time may be measured by computing the time between when the stimulus appears and when the response occurs. An average response time may be calculated for each level, averaging the reaction times for each trial. Variances and standard deviations may be calculated as well.

2. For each level of difficulty (when applicable), a summary of mean accuracy and mean and standard deviation of response times are generated.

3. For certain tests, an aggregate accuracy score (composite score) is generated. For tests where timing is critical, a derived index is computed, by dividing accuracy by response time to account for the "speed-accuracy tradeoff." Standard deviation of reaction time outcome parameters are computed as the standard deviation of the reaction time across all trials in a level. Other test-specific outcome parameters are generated in a similar manner, as appropriate for the test.

4. Raw performance measures are converted into an IQ scale (based on 100, plus or minus a standard deviation of 15) or other standardized scale and are normalized relative to the performance of a population, based on age- and education-specific normative data, generated from healthy individuals in controlled clinical trials. Data relating to the population are accumulated prior to testing based on a sample size of at least 20 people, and are stored in a database which is easily accessible by the system. Populations are chosen for optimal normalization. For example, to avoid having too broad or too narrow an array of demographic profiles, populations within a variety of diagnoses associated with cognitive impairment are chosen and separated from populations of cognitively healthy individuals, and only cognitively healthy individuals are used for the normalization process. In addition, normalization may be done in an age- and education specific fashion to account for differences based on these criteria as well. Furthermore, data relating to the populations are updated at least once every few years so as to avoid providing outdated data.

5. Index scores are generated for each cognitive skill based on the battery of tests. The index score is an arithmetic combination of several selected normalized scores. For example, one index score may include within it a combination of various memory outcome measures. This type of score is more robust than a single measure since it is less influenced by spurious performance on any individual test. For example, a memory index score may be comprised of individual measures from a verbal and a non-verbal memory test, and may also include a delayed recognition component. An example of an algorithm for computing the index score, according to one preferred embodiment, is a linear combination of a specific set of memory measures. The selection of the member of the set of measures and the weighting of each member is based on the known statistical method of factor analysis. The resulting linear combination is then converted to a memory index score by calculating a weighted average.

Index scores may be graphed in two ways. For example, a score for memory is calculated, for example, as 103. The first graph shows the score as compared to the general population. The score of 103 is shown on the graph within the normal range for the general population. The general population may either be a random sampling of people, or alternatively, may be a selected group based on age, education, socio-economic level, or another factor deemed to be relevant. The second graph shows the score as compared to any previous results obtained from the same battery of tests on the same subject. This longitudinal comparison allows the clinician to immediately see whether there has been an improvement or degradation in performance for each particular index.

6. Global cognitive function scores are generated by combining individual matrices. In one embodiment, the global cognitive function score is an average of the index scores. As shown on the graph, the global cognitive function score is also graphed relative to a population and relative to previous results from the same individual.

Results may also be compared to a disease-specific metric. For example, if it is desired to determine whether an individual has normal memory loss for their age or whether their memory loss is due to a disease such as Alzheimer's, an MCI (mild cognitive impairment) score is calculated and compared to a normal population as well as a disease-specific population, immediately allowing the clinician to see what range the subject's performance fits into. Furthermore, several indices may be compared, so as to determine which index is the most significant, if any.

A specific example of a discriminating score is an MCI score, derived from six outcome parameters that span a range of cognitive domains and show good sensitivity and specificity for discriminating individuals with mild Alzheimer's disease from healthy elderly. For each of these outcome parameters, cutoffs for the best balance between sensitivity and specificity are identified based upon a cohort of patients drawn from the registry of a well-established tertiary care referral center for evaluation of memory complaints. Performance on each outcome parameter is scored as pass (0) or fail (1), depending upon whether it is above or below the cutoff, respectively. The total number of failures on the six outcome parameters is scaled to a 10-point scale to yield the MCI score. Based upon a reference sample, the 10-point scale is subdivided into a zone 100% specific for healthy elderly (0 to 2.5; no individuals with AD in this zone), a zone 100% specific for AD (7.5 to 10; no healthy individuals in this zone), and a middle zone (2.5 to 7.5; both healthy elderly and those with AD in this zone). It should be readily apparent that this discriminating score can be calculated in any number of ways, and that the description included herein is a preferred embodiment.

Thus, the practitioner receives a complete picture of the performance of the individual as compared to previous tests as well as compared to the general population, and can immediately discern what type of medical intervention is indicated. It should also be noted that at different points during the test itself, it may be determined that a specific test is not appropriate, and the tests will then be switched for more appropriate ones. In those cases, only the relevant scores are used in the calculation.

In a preferred embodiment, a set of performance ranges is included, rather than a simple rendering of normal or abnormal diagnosis. That is, calculation of several sub-ranges, such as abnormal, probably abnormal, probably normal and normal is done. At least three levels of information may be provided. First, results can provide a scale and interpretation to indicate the likelihood of general abnormality—not specific to a given disease or condition. Second, results can be provided to indicate the likelihood of a specific abnormality (disease or condition). Third, results can be provided to indicate a differential diagnosis.

A method for calculating various sub-ranges of performance in accordance with a preferred embodiment of the present invention is described. First, a database is formed as follows. Populations of known normal individuals and known diseased individuals are provided. These populations are classified as normal or diseased based on expert diagnoses provided by physicians based on patient history, physical examination, and ancillary laboratory or imaging data, as necessary. Large numbers of individuals (in the hundreds) from each of the populations are given tests such as the ones described herein for data collection. Tests may be administered based on a specific disease, such as, for example, Alzheimer's, wherein only the relevant tests are given to both the normal and the diseased populations and the resulting data classified as normal and pathological Alzheimer's results. Alternatively, tests may be administered for general cognition, wherein each of the tests described herein is used for data collection. Any suitable combination of tests may be used for different test batteries, and saved in a database for that particular test battery. Furthermore, data may be separated according to various demographic factors including age, education level, language, ethnicity, gender, handedness, socioeconomic status, world region or country of origin, world region or country of testing, history of prior computer use, degree of computer use, or various combinations thereof. Databases are updated on a regular basis. In a preferred embodiment, databases are updated at least twice a year. In alternative embodiments, databases are updated at least once every two or three years.

Gap measures are calculated for discrimination of normal versus disease for a given parameter. In a preferred embodiment, gap measures are calculated by subtracting results for diseased populations from results for normal populations. In alternative embodiments, other arithmetic calculations may be used, such as fractions, percentages and others. Gap measures may be calculated for individual measures within an individual disease category, or across several chosen measures within an individual disease category, or for an individual measure across several disease categories. Further, a gap measure of global cognitive score comparing performance for all abnormal diagnoses with performance of normal populations is calculated. The gap measure provides a raw number representing how far from the normal measurement an individual has to be in order to be categorized as abnormal, either for one specific domain with respect to one specific disease state (such as memory as an indicator of MCI, or memory as an indicator of dementia, for example), or for one domain with respect to all of the disease states (such as memory as a general indicator of abnormality), or for several domains with respect to one disease (such as various measurements as indicators of Parkinson's), or as a general categorization of normal versus abnormal.

Mean normative data is transformed into a known scale, such as, for example, a z-score or IQ type scale. In a preferred embodiment, the transformation is a linear transformation. The transformation used in the following description is a z-scale transformation, wherein the mean is set to zero, and the standard deviation is set to ±1. Thus, multiple standard deviations from the mean are defined, wherein one standard deviation from the mean is 1, half the value of the standard deviation from the mean is 0.5, etc. These redefined standard deviation values are referred to herein as spread values. Spread values can be any values indicating a distance from the mean, and are not limited to the z-score transformation described above.

Next, spread value cutoffs are categorized at 0.25; 0; −0.25; −0.5; −0.75; and −1, respectively. At each cutoff, each tested individual is classified as normal or abnormal based on the test results. This diagnosis is compared with the gold standard diagnosis, previously obtained for the individual by clinical experts. Preferably, the clinical experts are from reliable research centers. The comparison of the testing diagnosis with the gold standard diagnosis results in a data classification of either false positive (FP), false negative (FN), or correct classification. Correct classifications are those where the testing diagnosis and the gold standard diagnosis agree. FPs are those where the testing diagnosis is abnormal and the gold standard diagnosis is normal. FNs are those where the testing diagnosis is normal and the gold standard is abnormal. In a preferred embodiment, these classifications are obtained by generating a 2×2 crosstab wherein data from each individual is placed in one of the cells. One axis is for the gold standard abnormal and normal, and the other axis is for the testing classification abnormal vs. normal. Correct classifications are those where the gold standard and the computerized testing classification agree. FP is where computerized testing indicated 'abnormal', but the gold standard indicated 'normal. FN is where computerized testing indicated 'normal' and the gold standard was abnormal. A percentage of false positives and false negatives out of the total data collected is calculated for each index score at each cutoff. This procedure may be done for general cognitive ability, for a particular set of measures believed to be relevant to a specific disease diagnosis, or for one particular measure.

Three criteria a, b and c are then used to optimize and judge the most appropriate cutoff for each measure. Criterion a demands that the number of false positives is minimized, criterion b demands that the number of false negatives is minimized, and criterion c sets a best-balance between false positives and false negatives. Criterion a may be set, for example, to the number closest to 0.10, which allows for a 10% rate of false positives. Similarly, criterion b may be set to the number closest to 0.10, which allows for a 10% rate of false negatives. It should be readily apparent that these values may be set to any level, and that this determination will set a boundary between abnormal and possibly abnormal and between normal and possibly normal diagnoses respectively. Thus, the numbers can be set higher or lower for higher or lower tolerance levels of false diagnoses. Criterion c demands that an absolute value of the difference between the percentages of false positives and false negatives must be the smallest. That is, |p(FP)−p(FN)| is the smallest value. This value sets a border between possible abnormal and possible normal. By setting these boundaries, a clinician has the ability to determine normal or abnormal cognition within the "gray area" range (i.e. not clearly normal or abnormal) with greater or lower tolerance for false positives or false negatives, depending on the clinical needs.

In one embodiment, scores are corrected for intelligence level differences by providing separate intelligence data to the clinician. This allows results to be put into perspective. For example, a highly intelligent individual may show abnormality at a higher score than an individual of lower intelligence. Specifically, individuals are given a standard IQ test or a specially designed battery of computerized tests to independently measure intelligence. Results are either presented to the clinician along with the report, or are used to automatically adjust the score within the testing system. The final report can include both scores so as to provide the clinician with a more comprehensive picture of the individual.

Figure 10A:
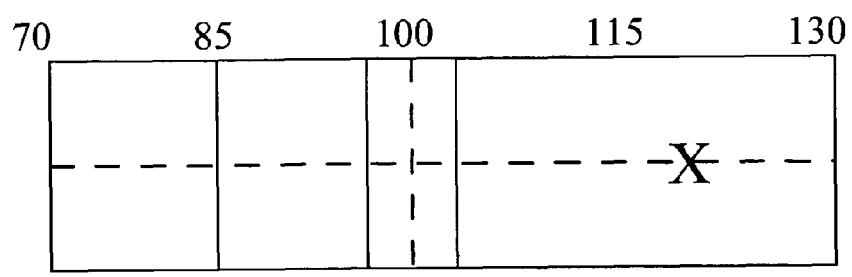
FIGS. 10A-B are graphical illustrations of results as presented to a clinician.
Figure 10B:
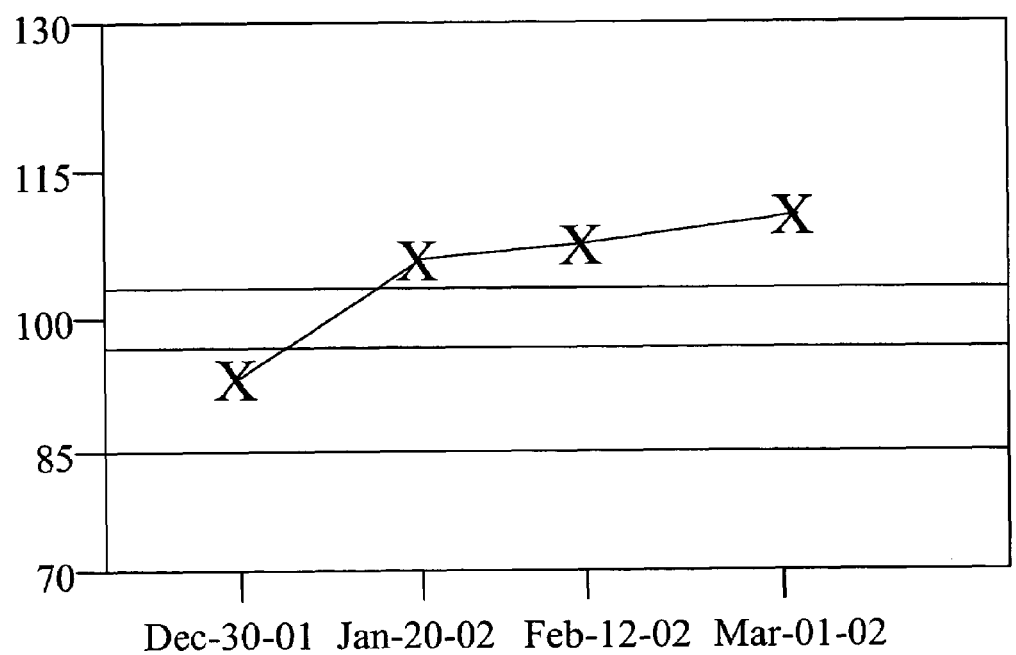

Reference is now made to FIGS. 10A and 10B, which are examples of graphical illustrations included in a sample report, showing the various sub-ranges as calculated according to a method such as the one described above. The clinician is able to use these results to help provide a diagnosis, based on the ranges and sub-ranges. Rather than simply defining a normal or abnormal diagnosis, the clinician is presented with multiple cut-offs and sub-ranges, each reflecting a different relative weighting of false positives and false negatives. Thus, for example, if it is particularly important not to misdiagnose healthy individuals (such as in a recommendation for a surgical procedure), the clinician may choose to tolerate the false negatives (that is, the number of abnormals diagnosed as normal) and to provide a diagnosis based on that tradeoff. Alternatively, in a case in which it is important to identify as many abnormal individuals as possible even at the expense of misdiagnosing normal individuals (such as in a screening procedure wherein further testing will subsequently be done), the clinician may choose to tolerate the false positives and to provide a diagnosis based on that tradeoff. These possibilities as well as a whole range in between are possible using the sample report with sub-ranges as shown.

As shown in FIG. 10A, a graph is presented showing the current test results. A graph such as the one shown in FIG. 10A may be generated for any individual index score, or for a global cognitive score, or both. For a given battery of tests, multiple graphs such as the one depicted in FIG. 10A may be included in one sample report. The graph enables the clinician to immediately discern the range and sub-range within which the result falls. That is, the clinician can determine whether, based on the score, the individual seems to fall within a normal range with a high probability, is likely within a normal range, is likely within an abnormal range, or falls within the abnormal range with a high probability.

Further, a graph such as the one depicted in FIG. 10B may be provided, in the event that at least one prior testing session has been recorded. As shown in FIG. 10B, previous results are graphed together with the current results, to provide the clinician with an overall picture of performance. Again, this type of graph may be provided for one or several indices, or for a global cognitive score, or both.

In preferred embodiments, the report would also include the patient's name and identification, date of birth, referring physician, and which testing battery is being used. The report would preferably also include a text summary of the results, and recommendations for the clinician.

Data reports may be sent to the clinician via any data transfer method, such as the Internet. All data is encrypted according to known techniques before being sent through public domains, so that privacy is assured. A system for sending test batteries as well as assessment reports or results data to a remote location is described in published U.S. Patent Publication No. 20030167149, for which a Notice of Allowance has been received and which is assigned to a common assignee of the present application and incorporated herein by reference in its entirety.

Quality Control

Automatic quality control features are included to ensure the integrity of the cognitive data. Full data security features, including firewall, triple DES encryption, secure socket layer, audit trails and password protection are included. Continuous checks are made of the local testing computer for adequate performance throughout the testing session, as it relates to accuracy of timing measurements. Automatic detection of missing data or data out of expected ranges is performed, and the system deals with such missing data accordingly. Automatic detection of data patterns that might be associated with computer malfunction is included. Personnel are immediately alerted upon detection of a potential technical error. Performance patterns that might indicate invalid participant performance are automatically detected. Suspicions of invalid results are sent to the tester.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Example 1

A study designed to assess the discriminant validity of some of the computerized tests described herein as compared with that of traditional neuropsychological tests is detailed below, (see Dwolatzky et al., "Validity of a novel computerized cognitive battery for mild cognitive impairment," BMC Geriatrics, 2003, 3:4).

Methods:

Participants were 98 elderly individuals, initially diagnosed as having mild cognitive impairment (MCI), mild Alzheimer's disease (AD), or as cognitively healthy, all according to well-known criteria and by consensus of evaluation teams led by dementia experts. A total of 30 individuals were in the MCI group, 29 individuals in the AD group, and 39 individuals in the healthy group. All groups were controlled for demographic and clinical characteristics.

All participants were given paper-based tests as well as a battery of computerized tests (the Mild Cognitive Impairment Battery) described in the present application. Specifically, standardized tests were administered as follows: memory tests included the Logical Memory subtest of the Wechsler Memory Scale, $3^{rd}$ edition (WMS-III) and the Rey Auditory Verbal Learning Test (RAVLT), Version 1. Tests of executive function included the Clock Drawing Test, the Trail Making Test (Part A), the Digit Symbol subtest of the Wechsler Adult Intelligence Scale, $3^{rd}$ edition (WAIS-III), and the Mental Control subtest of the WMS-III. Visual spatial skills were assessed with the Block Design subtest of the WAIS-III. Tests of verbal fluency included the Boston Naming test, the Controlled Oral Word Association (COWA) test, and the Similarities subscale of the WAIS-III.

The Mild Cognitive Impairment Battery administered to the participants included memory (verbal and non-verbal), executive function, visual spatial skills, verbal fluency, attention, information processing, and motor skills, in accordance with the tests described in the present application. Following administration of the computerized tests, performance indices were calculated as {accuracy/reaction time}*100, to account for both accuracy and reaction time. Tests were run in the same fixed order for all participants.

Data Analysis:

All statistics were computed with SPSS statistical software (SPSS, Chicago, Ill., USA). Two-tailed statistics were used throughout, and $p<0.05$ was considered significant. Receiver operating characteristic (ROC) analysis was used to evaluate the ability of the testing system's outcome parameters and traditional neuropsychological tests to discriminate participants with MCI from cognitively healthy elderly. Area under the curve (AUC), an index of effect size, was the primary result of the ROC analysis. For each measure, the AUC indicated the probability that a randomly selected individual with MCI would perform more poorly than a randomly selected cognitively healthy individual. An AUC of 0.050 indicated no better than chance discriminability, and an AUC of 1.00 indicated perfect discriminability. If the 95% confidence interval around an AUC included 0.50, the measure was unable to discriminate among MCI and healthy elderly at a significant level. Separate between-group comparisons were made on outcome parameters between mild MCI and mild AD. Given heterogeneous variances across these pairs of groups for numerous outcome parameters (Brown-Forsythe test, $p>0.05$), the non-parametric Mann-Whitney U was used to make the comparisons.

Results:

Results for discrimination of MCI from normal healthy elderly are summarized as follows. All memory, executive function, visual spatial skills and verbal fluency, and attention (Go-NoGo) outcome parameters discriminated significantly. The choice reaction time index did not discriminate significantly among MCI and cognitively healthy elderly. Medium and high-load information processing outcome parameters discriminated significantly, but the low load parameter did not. All motor skills outcome parameters did not discriminate significantly.

Results for discrimination of MCI and mild AD participants are summarized as follows. Significant differences were found between MCI and mild AD participants for memory, visual spatial, and verbal outcome parameters. Results were mixed for attention outcome parameters, such that timed Go-NoGo parameters did not significantly discriminate among MCI and mild AD, but the performance index from the choice reaction time test did.

Example 2

A study designed to identify normal/abnormal cutoffs for detecting mild impairment with a system such as the one described herein on the basis of research data from individuals with a wide array of cognitive diagnoses and an appropriate normative sample is detailed below.

Methods:

Analyses were conducted on data from 822 participants in controlled research studies using a computerized testing system such as the one described in the detailed description section above. Each participant received an expert diagnosis, which was taken as the gold standard. Expert diagnoses were based on the judgment of physicians relying on patient history, physical examination, and ancillary laboratory or imaging data, as necessary. For patients with multiple visits, only data from the first visit was included. Only patients whose primary language (i.e.,most comfortable using, language used most often) was available as a computerized test language were included.

The tests sampled various cognitive domains, including memory (verbal and non-verbal), executive function, visual spatial skills, verbal fluency, attention, information processing, and motor skills. All responses were made with the mouse or with the number pad on the keyboard. Patients were familiarized with these input devices at the beginning of the battery, and practice sessions prior to the individual tests instructed them regarding the particular responses required for each test.

Outcome parameters varied with each test. A performance index (computed as [accuracy/RT]*100) was computed for timed tests in an attempt to capture performance both in terms of accuracy and RT. To minimize differences in age and education and to permit averaging performance across different types of outcome parameters (e.g., accuracy, RT), each outcome parameter was normalized and fit to an IQ-style scale (mean: 100, SD: 15) in an age- and education-specific fashion.

Normalized subsets of outcome parameters were averaged to produce seven summary scores as follows, each indexing a different cognitive domain:

MEMORY: mean accuracies for learning and delayed recognition phases of Verbal and Non-Verbal Memory tests EXECUTIVE FUNCTION: performance indices (accuracy divided by RT) for Stroop test and Go/NoGo Response Inhibition (either standard or expanded) test, mean weighted accuracy for Catch Game VISUAL-SPATIAL: mean accuracy for 3-D Spatial Orientation test VERBAL: weighted accuracy for verbal rhyming test (part of Verbal Function test)

ATTENTION: mean reaction times for Go/NoGo Response Inhibition (either standard or expanded) and choice reaction time (a non-interference phase of the Stroop test) tests, mean reaction time for a low-load stage of Staged Information Processing Speed test, mean accuracy for a medium-load stage of Staged Information Processing Speed test INFORMATION PROCESSING SPEED: performance indices (accuracy divided by RT) for various low- and medium-load stages of the Staged Information Processing Speed test MOTOR SKILLS: mean time until first move for Catch Game, mean right and left inter-tap intervals for Finger Tap test These seven index scores served as the primary dependent variables for the present analysis. A Global Cognitive Score (GCS) computed as the average of these index scores served as a secondary dependent measure.

As batteries differed in the tests administered, data for all outcome parameters was not present for all patients. Missing outcome parameter data was also attributable to invalidation by quality control mechanisms triggered by response patterns indicative of poor compliance with test instructions (e.g., too many trials with the same response). Memory, Executive Function, Attention, and Motor Skills index scores were computed only if data was present for at least two of their constituent outcome parameters. The Information Processing Speed index score was computed only if data was present for at least three of its constituent outcome parameters, and the GCS was only computed only if data was present for at least three index scores.

Analysis:

For each index score, the difference in mean performance was computed between cognitively healthy (N=401) and each individual abnormal diagnosis. Cognitive domains predicted to evidence a performance decrement for specific diagnoses were identified on the basis of prior studies, and analyses restricted solely to these cells. Analyses were conducted both for each cell individually ('individual cell comparisons') and across all analyzed cells for a given index score ('crosscell comparisons').

As an example, for the Memory index score, only the following comparisons were analyzed: cognitively healthy vs. MCI, cognitively healthy vs. traumatic brain injury (TBI), cognitively healthy vs. mild dementia, and cognitively healthy vs. the combined group of MCI, TBI, and mild dementia patients.

Analyses were restricted to MCI, TBI, and mild dementia as memory impairment is a hallmark of these but not necessarily associated with the other abnormal diagnoses. Similarly, analyses of the Motor Skills index score were restricted to Parkinson's disease (PD) as motor impairment is characteristic of PD but not the other abnormal diagnoses. GCS performance for all abnormal diagnoses together (N=421) was compared with that of cognitively healthy individuals.

For each comparison, between-groups difference was tested and false positive (Type I error) and false negative (Type II error) rate (p[FP], p[FN]) computed at six normal/abnormal cutoffs relative to the normative mean: −1, −0.75, −0.5, −0.25, 0, and +0.25 SD units. The cutoff satisfying each of the following criteria was identified:

| Criterion | Condition |
| --- | --- |
| a | p(FP) closest to 0.10 |
| b | p(FN) closest to 0.10 |
| c | \|p(FP) − p(FN)\| smallest |

For each of the criteria, a cutoff was adopted for clinical use if criterion was met at that cutoff for the majority of comparisons tested. As an example, for the cognitively healthy vs. MCI comparison on the Memory index score, computation of p(FP) an p(FN) for the −1 SD cutoff was as follows.

A 2×2 table was constructed as below,

| | Memory IndexScore (−1 SD cutoff) | | |
|---|---|---|---|
| | Abnormal | Normal | TOTAL |
| Expert Diagnosis (Standard) Abnormal | 60 | 68 | 128 |
| Normal | 47 | 338 | 385 |
| | 107 | 406 | 513 | where Abnormal = MCI and Normal = cognitively healthy.

If letters are assigned to each of the cells as follows,

| | Memory IndexScore (−1 SD cutoff) | |
|---|---|---|
| | Abnormal | Normal |
| Expert Diagnosis (Standard) Abnormal | A | B |
| Normal | C | D |

$p(FP)=C/(C+D)$ and $p(FN)=B/(A+B)$. Substituting the actual values gives $p(FP)=47/(47+338)=0.12$ and $p(FN)=68/(60+68)=0.53$. Using these values, $|p(FP)-p(FN)|=|0.12-0.53|=0.41$. $p(FN), p(FP)$, and $|p(FP)-p(FN)|$ were computed in the same way for the −0.75, −0.5, −0.25, and 0 SD cutoffs to give the table below.

| Cutoff (SD Units) | p(FP) | p(FN) | |p(FP) − p(FN)| |
|---|---|---|---|
| −1 | 0.12 | 0.53 | 0.41 |
| −0.75 | 0.16 | 0.48 | 0.32 |
| −0.5 | 0.20 | 0.39 | 0.19 |
| −0.25 | 0.26 | 0.33 | *0.07* |
| 0 | 0.38 | 0.28 | 0.10 |
| +0.25 | 0.52 | *0.16* | 0.36 |

This table was then examined to determine the cutoff at which each criterion was met (bold and italicized cells). Across cutoffs, criterion a was met at −1 SD as 0.12 is the p(FP) value closest to 0.10. Criterion b was met at +0.25 SD, and criterion c was met at −0.25 SD. As indicated above, this procedure was run for each individual cell comparison and for each cross-cell comparison. The cutoff at which each criterion was most often met was identified, separately for individual cell comparisons and for cross-cell comparisons for each index score. Between-group tests were by independent samples t-test. If heterogeneity of variance was indicated by a significant Levene's test, the non-parametric Mann-Whitney U test was used instead. Two-tailed statistics were used throughout, and p<0.05 was considered significant. All statistics were computed with SPSS statistical software (SPSS, Chicago, Ill.).

Normalization:

Normalization was according to a normative sample consisting of 483 participants with an expert diagnosis of cognitively healthy in controlled research studies. Of the 401 cognitively healthy individuals in the present analysis, 383 were also part of the normative sample.

Data was normalized according to age group (less than 18, 18-50, 50-70, and above 70) and years of education (no more than 12 years versus more than 12 years).

For the expanded Go-NoGo test, normalization was according to a normative sample consisting of 66 cognitively healthy (mean age: 22.7±5.5 years; mean education: 11.8±2.8 years) participants. A total of 116 participants (mean age: 24.3±7.5 years; mean education: 12.3±3.3 years) in the present analysis received the expanded Go-NoGo test. Of these, 44 participants were cognitively healthy, all of whom were part of the normative sample.

Expanded Go-NoGo test data was normalized according to age (less than or equal to 23, or greater than 23).

In the event of a failed practice session, a score equivalent to 2 percentile units was assigned. This score was also assigned for performance index outcome parameters in the event of 0% accuracy on the actual test. To limit the influence of extreme outliers, actual test performance of poorer than −4 SD was replaced with the normalized score for −4 SD.

Results:

Robust (p<0.001) between-group differences were found for the vast majority of comparisons.

Individual Cell Comparisons

Criterion a: p(FP) Closest to 0.10

For all 21 individual cell comparisons, p(FP) was closest to 0.10 at −1 SD units.

Criterion b: p(FN) Closest to 0.10

For 16 of the 21 individual cell comparisons, p(FN) was closest to 0.10 at +0.25 SD. Criterion b was met at −0.75SD for 1 comparison (Memory, mild dementia), −0.25SD for 3 comparisons (executive function, mild dementia; verbal function, mild dementia; attention, schizophrenia), and at OSD for one comparison (executive function, schizophrenia).

Notably, at a cutoff of +0.25SD, p(FN) was less than 0.10 for these 8 comparisons.

Criterion c: |p(FP)−p(FN)| Smallest

For 13 of the 21 individual cell comparisons, |p(FP)−p(FN)| was smallest at −0.25 SD. Criterion c was met at −0.75 SD for 2 comparisons (memory, mild dementia; attention, schizophrenia), at −0.5 SD units for 4 comparisons (executive function, mild dementia; verbal function, mild dementia; information processing speed, TBI; information processing speed, mild dementia), and at 0 for two comparisons (Attention, PD; Attention, HLGD).

Cross-Cell Index Score and GCS Comparisons

Criterion a: p(FP) Closest to 0.10

For all 7 index score comparisons across abnormal diagnoses predicted to evidence a performance decrement (Table 3), p(FP) was closest to 0.10 at −1 SD units (Table 4). For the GCS comparison across all abnormal diagnoses, criterion a was met at −0.75 SD units. At a cutoff of −1 SD, p(FP) was less than 0.10 for this comparison.

Criterion b: p(FN) Closest to 0.10

For 6 of the 7 index score comparisons, p(FN) was closest to 0.10 at +0.25 SD. Criterion b was met at −0.25 SD for the Verbal Function index score comparison. At a cutoff of +0.25 SD, p(FN) was less than 0.10 for this comparison. For the GCS comparison, p(FN) was closest to 0.10 at +0.25 SD.

Criterion c: |p(FP)−p(FN)| Smallest

For 4 of the 7 index score comparisons, |p(FP)−p(FN)| was smallest at −0.25 SD. Criterion c was met at −0.5 SD for the Verbal Function and Information Processing Speed index score comparisons. |p(FP)−p(FN)| was smallest at 0 SD for the Motor Skills index score comparison. For the GCS comparison, criterion c was met at −0.25 SD.

Discussion:

The present analysis identifies −0.25 SD units (i.e., 96.25 normalized units) as a best-balance normal/abnormal cutoff, with equivalent severity of Type I and Type II errors (criterion c).

Across a range of abnormal diagnoses and summary measures anticipated to evidence impairment for those diagnoses, p(FP) and p(FN) were approximately equivalent at −0.25 SD. Given this cutoff, a score above 96.25 would be considered 'normal' and a score 96.25 or below 'abnormal'. While balanced at a cutoff of −0.25 SD, p(FP) and p(FN) were approximately 0.30. Hence, using this cutoff, a sizeable proportion of classifications in either the 'normal' or 'abnormal' range may be erroneous. Therefore, additional cutoffs were identified to reduce p(FP) in the 'abnormal' range (criterion a) and p(FN) in the 'normal' range (criterion b).

Across comparisons p(FP) was reduced to approximately 0.10 (criterion a) at a cutoff of −1 SD (i.e., 85 normalized units). Thus this cutoff was adopted to distinguish between 'abnormal' and 'probable abnormal'. A score 85 or below would be considered 'abnormal', and a score from 96.25 to 85 would be considered 'probable abnormal'.

Using this cutoff, there would be only very few erroneous classifications in the 'abnormal' sub-range. p(FN) is sizeable at −1 SD, but rather than 'normal', scores immediately above 85 are classified as 'probable abnormal' on the basis of the −0.25 SD cutoff (criterion c). Hence scores above 96.25 are not 'abnormal', but neither are they 'normal'. Rather, they are 'probable abnormal', a designation that aptly reflects the certainty of scores in this sub-range on the basis of p(FP) for criterion c.

Across comparisons, p(FN) was reduced to approximately 0.10 (criterion b) at a cutoff of +0.25 SD (i.e., 103.75 normalized units). Thus this cutoff was adopted to distinguish between 'normal' and 'probable normal'. A score above 103.75 would be considered 'normal', and a score from 96.25 through 103.75 would be considered 'probable normal'. With this cutoff, there would be hardly any misclassifications in the 'normal' sub-range. p(FP) is considerable at +0.25 SD, but rather than 'abnormal', scores 96.25 and immediately below are classified as 'probable normal' on the basis of the −0.25 SD cutoff (criterion c). Hence scores 96.25 and below are not 'normal', but neither are they 'abnormal'. Rather, they are 'probable 'normal', a designation indicative of the certainty of scores in this sub-range on the basis of p(FN) for criterion c.

Taken together, the sub-ranges defined by the present analysis constitute an additional clinical tool. Rather than simply defining a 'normal range', the present analysis defines a set of clinically relevant sub-ranges on the basis of relative error rates. The analysis utilizes an appropriate normative sample, drawn from the same controlled research studies as the cognitively impaired participants and including many of the cognitively healthy participants. Further, by defining multiple cutoffs and sub-ranges, each reflecting a different relative weighting of severity of false positives and false negatives, the analysis moves beyond the limitations of a traditional single-cutoff approach. Finally, as it based upon multiple abnormal diagnoses including many associated with only mild impairment, the set of sub-ranges is both general and sensitive for detection of impairment in varied clinical contexts.

The convention of using −1 SD to −2 SD as a normal/abnormal cutoff on neuropsychological tests and particularly for MCI detection may be analogous to the 'probable abnormal'/'abnormal' cutoff of −1 SD (criterion a) in the present analysis.

This cutoff is associated with a relatively low severity of false negatives and is consistent with objective deficit being only one criterion for MCI and part of a more extensive workup. With the set of sub-ranges defined by the present analysis, a score immediately above −1 SD is classified not as 'normal', but rather as 'probable abnormal', thus giving the clinician a more accurate picture of the cognitive status of the patient.

Alternatively, the conventional normal/abnormal cutoff of −1 SD to −2 SD may actually be analogous to the normal/abnormal cutoff of −0.25 SD. If so, the disparity between the two may be attributable to the loose definition of cognitively normal in traditional normative samples and their questionable suitability as reference groups for experimental research data. Indeed the present analysis employed a strict definition of cognitively healthy both for the normative sample and for the cognitively healthy group in the study sample. This served to ensure that only individuals who were truly cognitively healthy were part of these groups and, as the same criteria were applied to both groups, to optimize the congruity between them. Given the more rigorous definition of 'normal' and the greater correspondence between normative and study samples, the normal/abnormal cutoff is higher than for a research study employing a typical neuropsychological test and the probable normal zone tightly straddles the normative mean.

The present analysis was designed for wide applicability across cognitive diagnoses and summary measures. However, it is clear that the single set of cutoffs derived herein may not be ideal for all cognitive diagnoses and summary measures. Future analyses may therefore derive diagnosis- and index-score specific cutoffs to further improve clinical utility in settings with focused applications.

What is claimed is:

1. A method for processing data for a neurological parameter, the method comprising:
defining multiple performance zones, said defining multiple cutoff values calculated by comparing classifications of data from computerized cognitive tests with an independent classification; calculating a number of false positives and false negatives from said comparison; and choosing a first cutoff value based on a first cutoff criterion for numbers of false positives or false negatives and a second cutoff value based on a second cutoff criterion for numbers of false positives or false negatives;
providing a computerized cognitive test to a user;
collecting data from said computerized cognitive test;
calculating a score for said neurological parameter based on said collected data; and
placing said calculated score in one of said defined multiple performance zones.

2. The method of claim 1, further comprising providing a report showing said defined multiple performance zones and said placed calculated score.

3. The method of claim 1, wherein said multiple performance zones include a normal zone, an abnormal zone, and at least one additional zone in between said normal zone and said abnormal zone.

4. The method of claim 1, wherein said multiple performance zones are based on at least one of: a 10 point scale, a z-scale, an IQ scale or a linear transformaton thereof.

5. The method of claim 4, wherein said multiple performance zones are based on a 10 point scale and wherein a first cutoff value is between 6 and 9 and a second cutoff value is between 1 and 4.

6. The method of claim 4, wherein said multiple performance zones are based on a z-scale and wherein said multiple cutoff values are numbers between −1 and 1.

7. The method of claim 1, wherein said defining multiple performance zones further comprises choosing a third cutoff value based on a third cutoff criterion for numbers of false positives or false negatives.

8. The method of claim 1, further comprising normalizing said collected data to a reference population and standardizing said collected data to a standard scale, and wherein said calculating a score comprises calculating a score based on said normalized and standardized collected data.

* * * * *